US006688476B2

(12) United States Patent
Breillatt, Jr. et al.

(10) Patent No.: US 6,688,476 B2
(45) Date of Patent: Feb. 10, 2004

(54) FILTER ASSEMBLY HAVING A FLEXIBLE HOUSING AND METHOD OF MAKING SAME

(75) Inventors: Julian P Breillatt, Jr., Mundelein, IL (US); John C Burnham, Lake Zurich, IL (US); Allen R Wons, Antioch, IL (US); Randy Murphy, Pleasant Prairie, WI (US); Daryl R Calhoun, Green Oaks, IL (US); Daniel R Lynn, Spring Grove, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/084,605

(22) Filed: Feb. 27, 2002

(65) Prior Publication Data

US 2003/0000886 A1 Jan. 2, 2003

Related U.S. Application Data

(63) Continuation of application No. 10/055,862, filed on Jan. 23, 2002, now Pat. No. 6,601,710, which is a continuation of application No. 09/295,048, filed on Apr. 20, 1999, now abandoned, which is a continuation-in-part of application No. 08/697,270, filed on Aug. 21, 1996, now Pat. No. 6,032,807, which is a continuation of application No. 08/558,458, filed on Nov. 16, 1995, now abandoned, which is a continuation of application No. 08/392,297, filed on Feb. 22, 1995, now abandoned, which is a continuation of application No. 08/173,608, filed on Dec. 22, 1993, now abandoned.

(51) Int. Cl.$^7$ ............................................. B01D 27/08

(52) U.S. Cl. ...................... 210/435; 210/232; 210/252; 422/101; 422/102; 604/408

(58) Field of Search .................................. 210/232, 435, 210/252; 422/101, 102; 604/408

(56) References Cited

U.S. PATENT DOCUMENTS

| 3,506,130 A | 4/1970 | Shave |
| 3,747,769 A | 7/1973 | Brumfield |
| 4,025,618 A | 5/1977 | Garber et al. |
| 4,035,304 A | 7/1977 | Watanabe |
| 4,066,556 A | 1/1978 | Vaillancourt |
| 4,113,627 A | 9/1978 | Leason |
| 4,148,732 A | 4/1979 | Burrow et al. |

(List continued on next page.)

FOREIGN PATENT DOCUMENTS

| EP | 155 003 | 9/1985 |
| EP | 0155055 | 9/1985 |

(List continued on next page.)

OTHER PUBLICATIONS

Excerpts from Opposition involving EP 684,867 (European Counterpart of Lynn US 5,591,337), including (1) Notice of Opposition; (2) Response to Opposition; (3) Statement Replying to Response; (4) Reply to Statement in Response, and (5) Opposition Decision.

Primary Examiner—John Kim
(74) Attorney, Agent, or Firm—Daniel D. Ryan; Bradford R. L. Price; Amy L. H. Rockwell

(57) ABSTRACT

A fluid filter assembly for filtering fluids such as blood is described. The assembly includes first and second filter housing elements formed by an injection molding process. Each element is flexible and includes a peripheral flange formed thereabout and a fluid communicating port formed therein. Filter media, such as a filter membrane, is sealed between the mating flanges of two elements. The fluid filter assembly is capable of collapsing and expanding during the filtration process depending upon the composition of the fluid passed there through. A method for making the filter assembly and systems for using the filter assembly are also disclosed.

3 Claims, 14 Drawing Sheets

U.S. PATENT DOCUMENTS

| | | |
|---|---|---|
| 4,157,967 A | 6/1979 | Meyst et al. |
| 4,170,056 A | 10/1979 | Meyst et al. |
| 4,193,876 A | 3/1980 | Leeke et al. |
| 4,211,825 A | 7/1980 | Shipman |
| 4,234,026 A | 11/1980 | Bayham |
| 4,235,233 A | 11/1980 | Mouwen |
| 4,240,481 A | 12/1980 | Bayham |
| 4,268,338 A | 5/1981 | Peterson |
| 4,305,443 A | 12/1981 | Bayham |
| 4,380,484 A | 4/1983 | Repik et al. |
| 4,412,835 A | 11/1983 | Spencer |
| 4,417,753 A | 11/1983 | Bacehowski et al. |
| 4,425,177 A | 1/1984 | Shinno |
| 4,437,472 A | 3/1984 | Naftulin |
| 4,460,366 A | 7/1984 | Shinno |
| 4,466,888 A | 8/1984 | Verkaart |
| 4,482,585 A | 11/1984 | Ohodaira et al. |
| 4,493,705 A | 1/1985 | Gordon et al. |
| 4,507,123 A | 3/1985 | Yoshida |
| 4,539,793 A | 9/1985 | Malek |
| 4,707,402 A | 11/1987 | Thorsrud |
| 4,767,541 A | 8/1988 | Wisdom |
| 4,770,295 A | 9/1988 | Carveth et al. |
| 4,798,578 A | 1/1989 | Ranford |
| 4,857,129 A | 8/1989 | Jensen et al. |
| 4,863,603 A | 9/1989 | Lehmann et al. |
| 4,892,537 A | 1/1990 | Carmen et al. |
| 4,892,603 A | 1/1990 | Lustig et al. |
| 4,892,604 A | 1/1990 | Measells et al. |
| 4,894,107 A | 1/1990 | Tse et al. |
| 4,900,389 A | 2/1990 | Schnell et al. |
| 4,900,441 A | 2/1990 | Graus et al. |
| 4,950,347 A | 8/1990 | Futagawa |
| 4,954,251 A | 9/1990 | Barnes et al. |
| 4,976,851 A | 12/1990 | Tanokura et al. |
| 4,997,577 A | 3/1991 | Stewart |
| 5,049,146 A | 9/1991 | Bringham et al. |
| 5,055,198 A | 10/1991 | Shettigar |
| 5,066,290 A | 11/1991 | Measells et al. |
| 5,180,504 A | 1/1993 | Johnson et al. |
| 5,190,657 A | 3/1993 | Heagle et al. |
| 5,225,014 A | 7/1993 | Ogata et al. |
| 5,269,924 A | 12/1993 | Rochat |
| 5,306,269 A | 4/1994 | Lewis et al. |
| 5,316,678 A | 5/1994 | Heaslip |
| 5,360,498 A | 11/1994 | Blomqvist et al. |
| 5,420,962 A | 5/1995 | Bakke |
| 5,435,878 A | 7/1995 | Delmar et al. |
| 5,449,428 A | 9/1995 | Desmarais et al. |
| 5,472,605 A | 12/1995 | Zuk, Jr. |
| 5,476,587 A | 12/1995 | Kuroki et al. |
| 5,489,385 A | 2/1996 | Raabe et al. |
| 5,507,904 A * | 4/1996 | Fisher et al. ................ 156/252 |
| 5,527,472 A | 6/1996 | Bellotti et al. |
| 5,556,541 A | 9/1996 | Ruschke |
| 5,575,880 A | 11/1996 | Strassberg |
| 5,580,349 A | 12/1996 | Thor et al. |
| 5,591,337 A | 1/1997 | Lynn et al. |
| 5,601,730 A | 2/1997 | Page et al. |
| 5,683,768 A | 11/1997 | Shang et al. |
| 5,688,460 A | 11/1997 | Ruschke |
| 5,707,520 A | 1/1998 | Kuroki et al. |
| 5,724,988 A | 3/1998 | Dennechey et al. |
| 5,728,249 A | 3/1998 | Kinsey, Jr. et al. |
| 5,728,306 A | 3/1998 | Breillatt, Jr. et al. |
| 5,736,719 A | 4/1998 | Lawson et al. |
| 5,772,880 A | 6/1998 | Lynn et al. |
| 5,779,902 A | 7/1998 | Zuk, Jr. |
| 5,853,577 A | 12/1998 | Gizowski et al. |
| 5,858,016 A | 1/1999 | Bacehowski et al. |
| 5,902,490 A | 5/1999 | Zuk, Jr. |
| 5,976,300 A | 11/1999 | Buchanan et al. |
| 6,010,633 A | 1/2000 | Zuk, Jr. et al. |
| 6,015,500 A | 1/2000 | Zuk, Jr. |
| 6,032,807 A | 3/2000 | Sternberg et al. |
| 6,168,718 B1 | 1/2001 | Sutter et al. |
| 6,251,292 B1 | 6/2001 | Zuk, Jr. |
| 6,274,055 B1 | 8/2001 | Zuk, Jr. |

FOREIGN PATENT DOCUMENTS

| | | |
|---|---|---|
| EP | 0 328 038 A2 | 8/1989 |
| EP | 0365676 | 5/1990 |
| EP | 0516846 | 12/1992 |
| EP | 0 521 222 A1 | 1/1993 |
| EP | 0 525 493 A1 | 2/1993 |
| EP | 0 526 678 A1 | 2/1993 |
| EP | 0526678 B1 | 2/1993 |
| EP | 0 614 675 A1 | 9/1994 |
| EP | 0 654 303 A1 | 5/1995 |
| EP | 0 679 490 A2 | 11/1995 |
| EP | 0684867 | 3/1999 |
| WO | WO 95/17237 | 12/1994 |
| WO | WO95/07818 | 3/1995 |

* cited by examiner

FILTER ASSEMBLY HAVING A FLEXIBLE HOUSING AND METHOD OF MAKING SAME

RELATED APPLICATIONS

This application is a continuation of U.S. patent application Ser. No. 10/055,862 filed Jan. 23, 2002, now U.S. Pat. No. 6,601,710, which is a continuation of U.S. patent application Ser. No. 09/295,048, filed Apr. 20, 1999, abandoned, which is a continuation-in-part of U.S. patent application Ser. No. 08/697,270 filed Aug. 21, 1996, (now U.S. Pat. No. 6,032,807), which is a continuation of U.S. patent application Ser. No. 08/558,458, filed Nov. 16, 1995, abandoned, which is a continuation of U.S. patent application Ser. No. 08/392,297, filed Feb. 22, 1995, abandoned, which is a continuation of U.S. patent application Ser. No. 08/173,608, filed Dec. 22, 1993, abandoned.

FIELD OF THE INVENTION

The present invention relates to an improved filter device for filtering, entrapping air, and preventing foaming in fluids, such as biological matter, including whole blood or blood components. More specifically, the invention relates to a filter assembly having an injection molded filter housing and a method of making a filter housing for performing the same. The invention may be used in blood collection and processing systems for removing leukocytes from whole blood, red blood cells, plasma, and platelets prior to transfusion or long term storage.

BACKGROUND OF THE INVENTION

It is common in the formation of medical and laboratory filters, such as blood filters or blood filtration housings containing filters, to form filter housings for filter media from one or more sheets of flexible polyvinyl chloride (PVC) material. It is also common to manufacture filter housings from rigid plastics such as acrylic, polypropylene, or a similar material.

Many types of devices are commercially available for separating whole blood components. Some machines are fully automated while others rely on manual operations performed by technicians. On a gross level, blood components include plasma (water and protein), red blood cells, leukocytes, and platelets. Filter media is commercially available to filter leukocytes from blood. A filter pad media for filtering leukocytes from blood cells is disclosed in U.S. Pat. No. 5,591,337, commonly owned by the assignee hereof.

While filter housings manufactured from flexible PVC material offer the benefit of having a flexible housing, it has been heretofore difficult to provide an efficient and reliable method for forming an inlet port and an outlet port in the filter housing. Prior art filter housings made from one or more sheets of PVC material have taught the formation of the port along the peripheral seal of the respective PVC material sheet edges. Typically, a short piece of tubing is used as the port. See, for example, U.S. Pat. No. 4,035,304 to Watanabe issued Jul. 12, 1977 and entitled Blood Filtering Bag. However, it is difficult to form a complete and reliable seal at the junction of the PVC material sheets and the tubing that serves as the port. Both an incomplete seal, as well as a weak seal can lead to fluid leaking from the filter assembly during the filtering process.

Introducing fluid into a filter housing at the seal of its panels or sheets is also less desirable when the flow characteristics of the fluid across the filter media are important (e.g. laminar flow or even flow across the filter media). If the fluid enters the housing immediately adjacent the filter media, the bubble strength of the filter media may be quickly surpassed by increased blockage of the filter media with filtered particulate and the resulting increased pressure within the filter housing may cause the filter media to rupture or burst. This is a very undesirable result in that it is difficult, if not impossible to immediately detect a ruptured filter membrane. Alternatively, increased blockage of the filter media may lead to turbulent fluid flow through the filter assembly. Many fluids react poorly to turbulent flow.

A similar prior art filter is taught in published European Patent Publication No. 0 516 846 to Sakamoto published Dec. 9, 1992 and entitled Bag-Like Filter. This application teaches the formation of filter housings from heat-fusible polyethylene films. In one embodiment the inlet and outlet ports are formed from polyethylene tubing fused between the film and the filter at their edges. Alternatively, separate inlet and outlet ports having a construction similar to a valve placed in a tire tube may be fused through an opening formed in the central regions of the film sheets.

Other prior art devices, such as U.S. Pat. No. 5,507,904, commonly owned by the assignee hereof, teach the formation of the inlet and outlet ports in the wall of a thermoplastic sheet filter housing by first forming a slit in the filter housing wall, inserting a separate tube through the slit and heating the mating materials to fuse the tube and sheet. While providing a very reliable filter assembly, extra care must be taken during the manufacturing process to ensure that the slit is not too large, the tube is properly placed prior to heating, and a good seal is formed around the tubing-wall junction. Some prior art filter assemblies do not include positive stops for the conduits attached to their filter ports. Without a stop, the possibility exists that the rubber or plastic conduit may be inserted too far into the port, thereby possibly damaging or piercing the filter media. In addition, if solvent is used to bond the conduit to the port, the solvent may contact and thereby degrade the filter media.

Filter housings molded from hard plastics such as acrylic allow for the formation of the inlet and outlet ports at almost any location along the wall or panel of the filter housing. The location is primarily limited only by the sophistication of the mold or die. However, the resulting filter assemblies have the drawback that they are not flexible and thus cannot substantially prevent a phenomenon common in fluid filtering processes known as "foaming." It is also sometimes necessary to centrifuge a blood container having a filter device attached thereto. A hard plastic filter housing may puncture or damage the blood container during the centrifuge process.

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Automated centrifugal blood collection systems and manual systems composed of multiple, interconnected plastic bags have met widespread use and acceptance in the collection, processing and storage of these blood components. In the United States, these systems are subject to regulation by the government. For example, the plastic materials from which the bags and tubing are made must be approved by the government. In addition, the maximum storage periods for the blood components collected in these systems are prescribed by regulation.

In the United States, whole blood components collected in a non-sterile, or "open", system (e.g. one that is open to communication with the atmosphere) must, under governmental regulations, be transfused within twenty-four hours. However, when whole blood components are collected in a sterile, or "closed", system (e.g., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove leukocytes is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove leukocytes is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline leukocyte filtration device is used. The filtration can thereby be accomplished in a closed system. However, the filtration processes associated with these arrangements require the extra step of wetting the filtration device before use with a red blood cell additive solution or the like. This added step complicates the filtration process and increases the processing time.

Other systems and methods for removing leukocytes in the context of closed, multiple blood bag configurations are described in Stewart U.S. Pat. No. 4,997,577. In these filtration systems and methods, a transfer assembly dedicated solely to the removal of leukocytes is used. The transfer assembly is attached to a primary blood collection container. The transfer assembly has a transfer container and a first fluid path leading to the transfer container that includes an inline device for separating leukocytes from red blood cells. The transfer assembly also has a second fluid path that bypasses the separation device. Using these systems and methods, leukocytes are removed as the red blood cells are conveyed to the transfer container through the first fluid path. The red blood cells, now substantially free of leukocytes, are then conveyed from the transfer container back to the primary collection container for storage through the second fluid path, this time bypassing the separation device.

A need still exists for an improved biological matter filter housing that is flexible and that includes an inlet or an outlet port integrally formed in the housing. A need exists for an improved filter housing capable of trapping air and preventing foaming of the fluid or blood passed through the filter. A need also exists for a form of a fluid filter having an inlet and an outlet formed tangentially in a flexible wall of the filter assembly. A need exits for an improved flexible filter housing having integral ports including positive stops for conduits connected to the filter also exists. Because these types of devices are often used only once (e.g. disposable) a need exists for an efficient, reliable and low cost method of making the filter assembly.

SUMMARY OF THE INVENTION

It is a principle object of the present invention to provide an improved filter device having a body defined by at least one injection molded, flexible filter housing element sealed to form an interior chamber. A filter medium is located within the chamber. The housing element has at least one port integrally molded therein. The integrally formed ports are tangential or substantially tangential to the filter housing walls and parallel to the filter medium.

In one embodiment, a filter device is provided and defined by at least one injection molded housing element having a flexible portion formed therein and sealed along edges thereof to form an interior cavity. A filter membrane is sealed within the cavity. At least one port, in fluid communication with the interior cavity, is integrally molded in the flexible portion. In a specific application, the port is positioned tangentially with respect to the flexible portion and the filter device is positioned horizontally with respect to the port.

In another embodiment the filter device comprises first and second generally flexible injection molded filter housing elements, each element having a flange formed about a periphery thereof and a domed portion formed therein. At least one port is molded in the domed portion. The filter housing elements arranged along their respective flanges to form an interior cavity and a filter membrane, having an outer periphery, is positioned between the filter housing elements. The first filter housing element flange, the filter membrane outer periphery and said second filter housing element flange are sealed together to form an interior cavity. Each port is in fluid communication with the interior cavity.

In another embodiment, the invention includes a container comprising an injection molded sheet having a substantially flexible portion integrally molded therein. The sheet is sealed along an edge after injection molding forming an interior chamber and at least one port is integrally formed in the flexible portion of the sheet. The port is in fluid communication with the interior chamber.

In yet further embodiments, a blood processing system is disclosed including a first bags, a second bag, and tubing providing communication between the two bags and including a blood filter or device of a type described above.

For example, the invention may be utilized in a multiple container blood collection system for conveniently processing the various components of blood. In such a system, the filter device of the present invention performs the function of separating the undesired matter, e.g., leukocytes, during processing. The system is arranged so that some blood components can be conveyed through the filter device, while other components can be readily conveyed along other paths that bypass the filter device.

An important aspect of the invention is that the filter housing element or elements are flexible thus allowing the filter device to expand and contract during the filtration process. In a preferred embodiment, the filter housing elements are dome-like in structure and the inlet or outlet port is molded in a central region of the dome. Due to its flexible structure, the filter device is capable of minimizing foaming of the fluid passed therethrough. The volume of the interior chamber is capable of increasing and decreasing its volume during the filtration process. While the filter medium is initially spaced a predetermined distance from the housing element, this distance may also change during the filtration process.

Another important aspect of the invention is that the filter device is capable of trapping air while in a horizontal orientation. In this orientation, the inlet port is positioned on the upper surface of the device and the outlet port is positioned on the lower surface. Accordingly, the present invention is well suited for applications on horizontal planes (e.g. the top panel of an instrument).

Yet another important aspect of the invention is that each filter element is injection molded thus producing a unitary, single filter element including a flexible portion and an integrally molded fluid port. The fluid ports include a port opening extending from the exterior of the element, through its flexible portion and into the element interior. The filter device inlet and outlet ports may include structure for limiting the insertion of a conduit therein. In a preferred embodiment, the filter elements may be molded from a thermoplastic material, such as polyvinyl chloride.

The filter media or medium enclosed within the filter device may be any of a great number of known filtration materials. As one example, the filter medium may comprise a polyester mesh material. In a specific application of the filter device, the filtration material is may be selected to remove undesirable materials, such as leukocytes, from whole blood, red blood cells, platelet rich plasma, platelet poor plasma or platelet concentrate. Examples of these filtration materials can be found in the following patents: U.S. Pat. Nos. 5,591,337, 5,089,146, 4,767,541, 5,399,268, 5,100,564, 4,330,410, 4,701,267, 4,246,107, 4,936,998 and 4,985,153. Each of these patents is incorporated herein by reference.

In accordance with a related aspect, the possibility of damaging or piercing the filter medium is eliminated by the inclusion of structure within the port opening that forms a stop. This aspect is particularly important when it is desirable to connect a conduit to the filter assembly using only an interference fit between the conduit and the port opening.

The first and second filter housings may be identical to one another. In this manner, the orientation of the filter ports can be readily positioned during the manufacturing process in the same direction or in opposed directions, depending upon the fluid to be passed through the filter, the filter medium and/or the location and application constraints of the filter device.

In accordance with an important specific application of the invention, the filter device may be incorporated into an apparatus for collecting and separating the various components of whole blood, e.g. red blood cells, platelets and blood plasma. The apparatus may be an automated blood separation apparatus or manual apparatus.

In accordance with another aspect of the invention, an injection molding die is provided to mold from a thermoplastic material filter housing elements, each having a flange portion, a flexible central region and an integral port. A second pair of opposed dies is provided to seal filter media between first and second filter housing elements. The dies, which are formed of an electrically conductive material are positioned so that the first housing element, filter media, and a second housing element are placed between said dies. When RF energy is transmitted to the flange portions of the first and second filter housings through the conductive dies, the thermoplastic material is caused to soften or melt and to flow to seal the periphery of the filter media between the housing elements.

In a preferred method of forming the fluid filter device from a thermoplastic material, the method comprises the steps of injection molding first and second flexible filter housings, each housing having a port integrally formed therein and having a periphery thereabout; placing a filter membrane between said first and second filter housing peripheries; and sealing along the periphery of the filter housing to form a fluid tight enclosure. In addition, the resulting enclosure may be trimmed in a cutting die to produce a more aesthetically pleasing filter device.

The fusing or sealing step may be conducted by placing the metallic dies on opposite sides of the filter housings and applying energy to the peripheries to dielectrically heat said peripheries to cause softening and sealing thereof. Alternatively, the fusing or sealing step may be conducted by the application of radio frequency energy.

Multiple filter housing elements may be molded and multiple filter housing assemblies may be formed at the same time. Utilizing this method a third cutting die is provided to individually cut each completed filter assembly from a carrier web.

Further advantages and aspects of the invention will be apparent from the following detailed description and accompanying drawings.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

Figure 7:
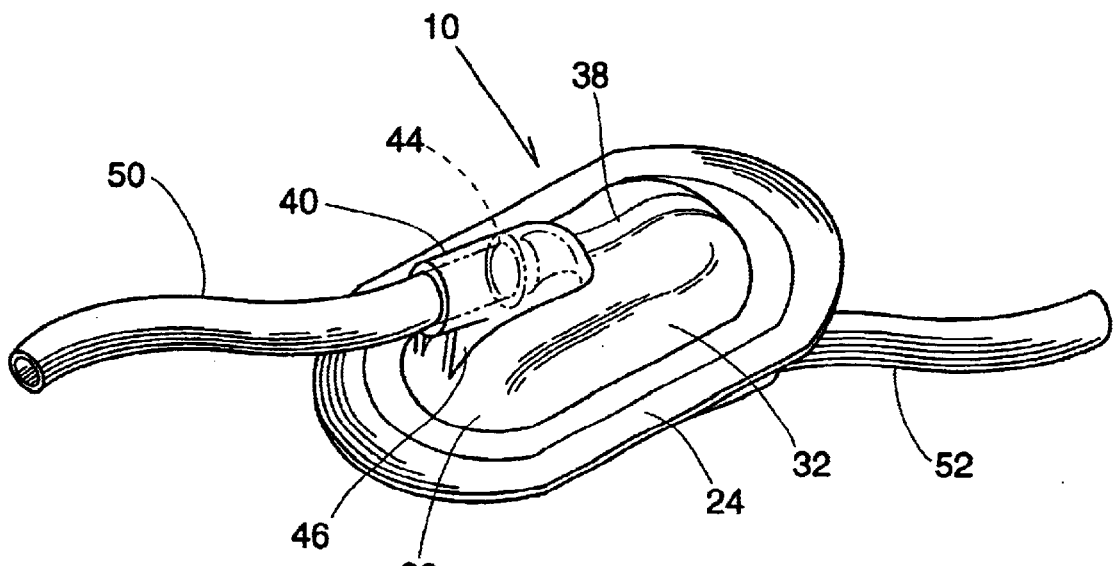
FIG. 7 is a perspective view of the filter assembly connected to inlet and outlet fluid conduits.

Referring more particularly to the drawings there is seen in FIG. 7 a filter assembly 10 used, for purposes of illustration only, to filter blood or blood components, e.g., red blood cells or platelet poor plasma in a manual or automated blood processing system during processing or before being returned to a donor from a blood separation apparatus. Two or more conduits, such as conduits 50 and 52 supply unfiltered blood to and convey filtered blood from the filter assembly 10 respectively. Filter media, not shown in FIG. 7, is contained within filter assembly 10. Blood filtration is only one application of the invention and is not intended to be a limitation of the present invention. Numerous other applications of the invention will be apparent to those skilled in the art.

Referring now to FIGS. 1 through 5, the preferred embodiment of filter assembly 10 can be seen to include first and second filter housing elements 20 and 22. As will hereinafter be appreciated, and as is apparent from FIGS. 2 and 3, the housing elements 20 and 22 are identical. Each housing element 20 and 22 includes a flange 24 formed about its periphery 26. A domed region 30 is formed within the flange area 24. The filter housing elements 20 and 22 are arranged, as will be described in greater detail, so that their domed regions 30 form and define an interior filter cavity 32.

Figure 1:
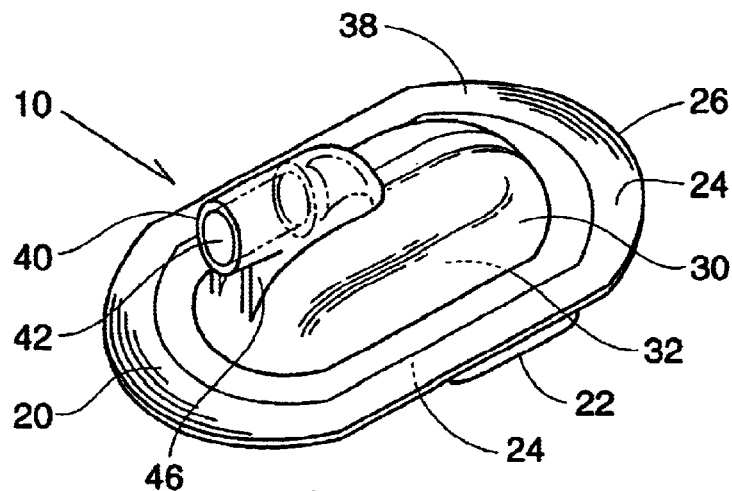
FIG. 1 is a perspective view of the filter assembly.
Figure 2:
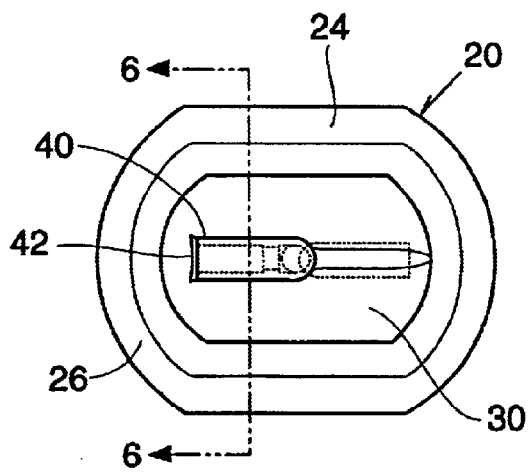
FIG. 2 is a top plan view of the filter assembly.
Figure 3:
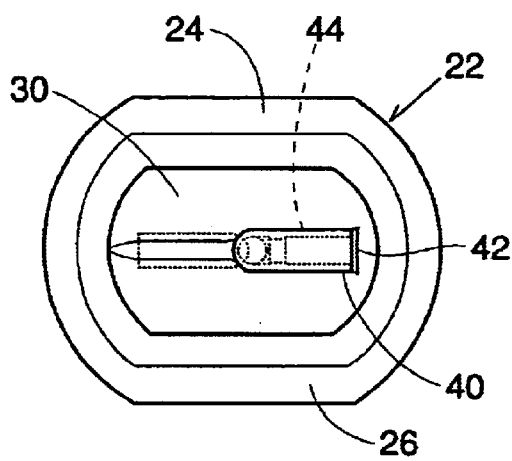
FIG. 3 is a bottom plan view of the filter assembly.
Figure 4:
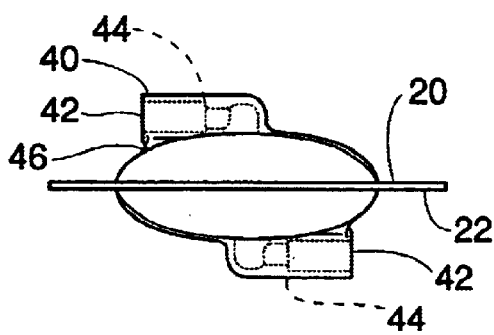
FIG. 4 is a right side elevation view of the filter assembly, the left side elevation view being a mirror image thereof.
Figure 5:
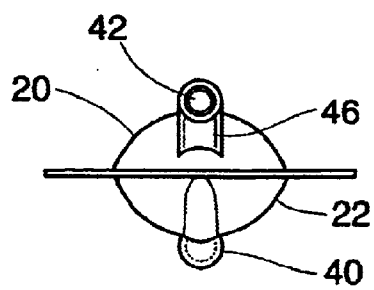
FIG. 5 is a front elevation view of the filter assembly.

The domed region 30 of each filter housing element 20 or 22 has at least one port 40 formed integral with the filter housing element. Port 40 includes an inlet 42 that passes though domed region 30 and that is in fluid communication with the interior cavity 32 of the filter assembly 10. Inlet 42 is sized to receive the end of a fluid carrying conduit, such as a flexible medical grade plastic (e.g., PVC) or rubber tube or hose. As best shown in FIG. 4, a shoulder 44 is formed within each inlet 42 to act as a conduit stop. The conduit stop prevents the insertion of conduit 50 or 52 too far into the filter assembly thereby possibly damaging or rupturing the filter media contained therein. A support rib 46 is formed beneath each port 40 to reinforce the port. Support rib 46 also strengthens the fluid communication openings between the port 40 and filter element dome 30 to prevent tearing of the port 40 from the dome region 30.

As will be discussed in greater detail below, each filter housing element 20 or 22 is preferably injection molded from a flexible thermoplastic material, such as flexible PVC material. The components of each element, including the flange 24, domed region 30, port 40 having opening 42, conduit stop 44, and support rib 46 are integrally molded as a single, unitary component. Unlike prior art devices, there is a minimized risk of fluid leaking at the junction of domed portion 30 and port 40.

Figure 6:
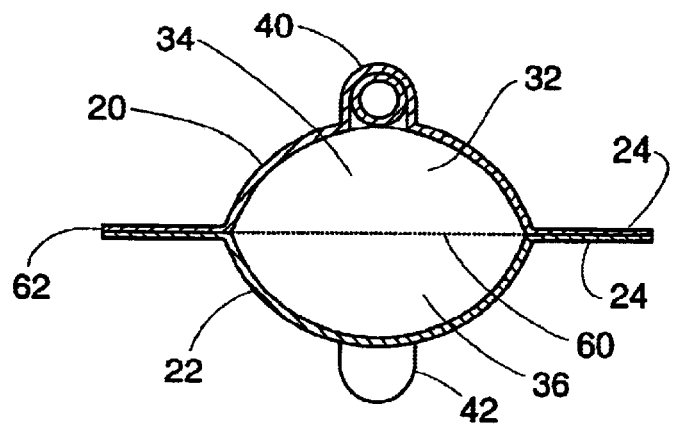
FIG. 6 is a cross sectional view taken along line 6—6 in FIG. 2 showing the filter media within the filter assembly.

Various types of filter media can be contained within the interior cavity 32. For example, a porous screen filter material, or a fibrous depth filter material, in single layers or in a multiple layer stack, can be used. An example of a filter media that may be sealed within the interior cavity 32 is best shown in FIG. 6. As shown, a membrane of filter media 60 having a periphery 62 is arranged and sealed between filter housing elements 20 and 22. The preferred filter media 60 is a soft polyester membrane having a 250 micron mesh. However, it is to be understood that any filter media, including other types of filter media membranes, could be used in the present invention. The preferred media is suitable for filtering particulate from red blood cells and platelet poor plasma before it is returned to a blood donor.

In a preferred embodiment, filter membrane 60 is heat sealed between the respective flanges 24 of housing element 20 and housing element 22 to form the interior region 32. The interior region 32 can be further divided into a first cavity 34 defined by housing element 20 and a first side 62 of filter membrane 60 and a second cavity 36 defined by housing element 22 and a second side 64 of filter membrane 60.

Again referring to FIG. 7, a fluid conduit 50 and 52, such as flexible medical grade plastic (e.g., PVC) or rubber tubing, can be attached to ports 40 by conventional means such as an interference fit or with the aid of a solvent. In a preferred application, fluid flows through opening 42 in port 40 formed in first or upper filter housing 20. The fluid then flows into first interior cavity 34, through filter media 60 and into second interior cavity 36. The fluid exits the filter assembly 10 by flowing through the opening 42 formed in port 40 of filter housing 22. The preferred embodiment of the filter assembly 10 depicts the location of the filter ports 40 at the top of the domed portion 30. The preferred embodiment 10 further depicts that the port 40 is formed substantially tangentially to the wall of the domed portion 30. The type of fluid to be filtered, whether or not the filter assembly must trap air within its interior region and the physical constraints of the filter application may dictate the orientation and location of port 40. It is to be understood that different locations and orientations of the port 40 may be made without deviating from the invention.

It is, thus, appreciated that the port 42 is formed in each filter housing element 20 generally tangential or parallel to the wall of the element. In the case of a filter assembly 10, the available surface area of the filter media 60 is maximized since the filter membrane itself extends to the periphery of the filter housing interior cavity 32 without adversely affecting fluid flow in and out of the filter assembly.

As best illustrated in FIG. 7 at reference numeral 38, the filter assembly 10 of the present invention is flexible and thus capable of collapsing (as shown) and expanding depending upon the fluid or combination of fluids flowing through the filter assembly. For example, if both a liquid, such as blood, and air are simultaneously flowing through a non-flexible or rigid filter assembly, a phenomenon known as foaming is likely to occur. The present invention 10 prevents this phenomenon by its ability to collapse when the volume of a non-compressible fluid (e.g. liquid) is decreased. Decreasing the volume of the interior cavity 32 prevents the foaming phenomenon from occurring.

The present filter assembly 10 also functions to entrap air within its interior cavity 32. The design lends itself to filter applications on horizontal planes such as the top panel of an instrument. By locating the inlet and outlet ports 42 in the central portion of each dome and provided the filter assembly 10 is positioned in a horizontal orientation (as shown in FIG. 7), any air contained within the fluid being passed through the filter 10 is trapped within the interior cavity 32. When the fluid enters the cavity 32 of the horizontally oriented filter assembly, the air will remain in an upper portion of the cavity 32 while the fluid will pass through the filter media 60 and toward the opposite or lower end of the cavity 32.

Although not specifically illustrated, it is within the province of the invention to provide a single flexible filter element that is adhered to a filter media or a non-flexible filter member. A port may be integrally formed in the filter element and a supply tube may be attached thereto. While different in structure, this alternative design would allow the filter assembly to perform both the filtration function and air entrapment function discussed above.

Figure 8:
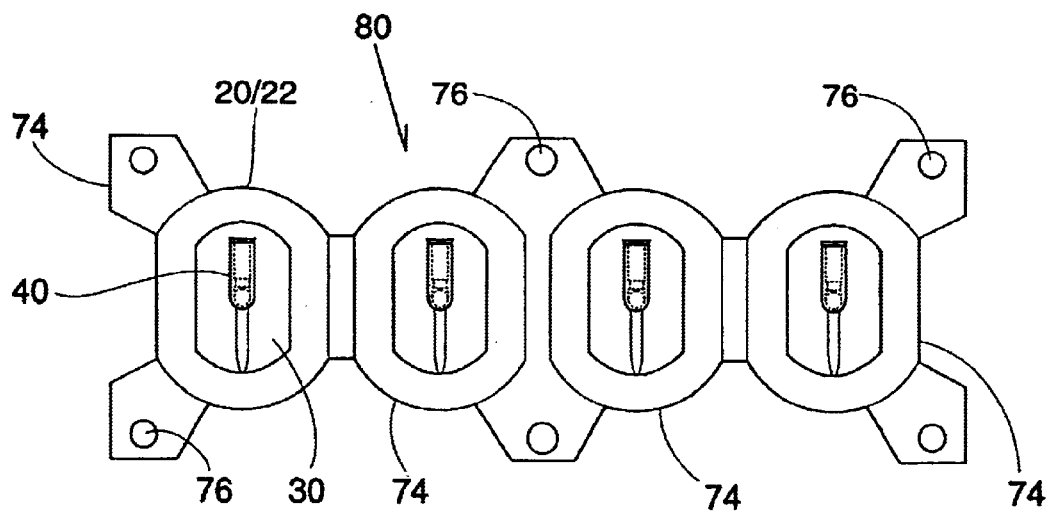
FIG. 8 is a top plan view of multiple filter housing bodies connected by a web.
Figure 9:
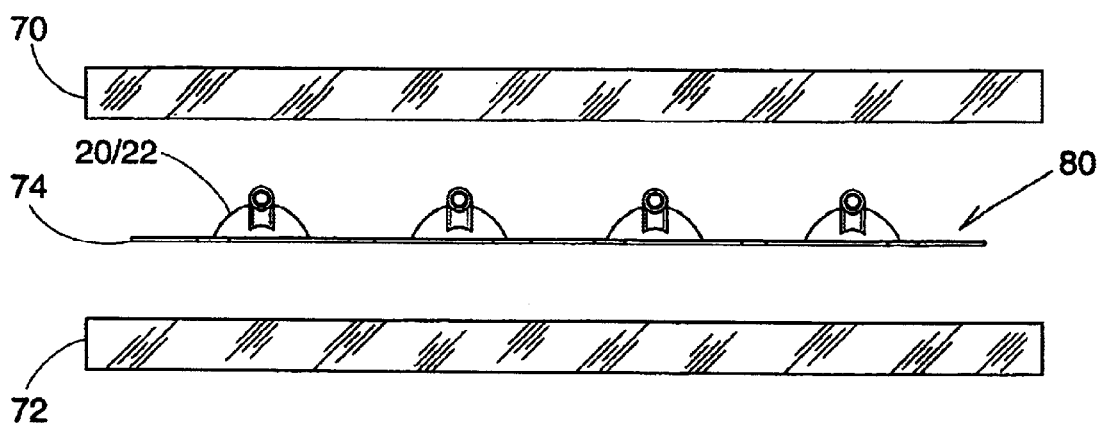
FIG. 9 is a front elevation view showing the multiple filter housing bodies being formed by an upper die and a lower die.

The filter assembly 10 of the present invention is typically a disposable or single use item. Therefore, it is important that the filter assembly 10 can be manufactured in an efficient and reliable method. Multiple filter housing elements 20 are preferably simultaneously formed by an injection molding process as illustrated in FIGS. 8 and 9. The following description contemplates four filter housing elements 20/22 being formed by an injection molding process and four filter assemblies 10 being formed in a subsequent assembly process. It is to be understood that any number of filter housing elements and filter assemblies could be formed at the same time without deviating from the present invention.

Referring specifically to FIG. 9, thermoplastic material, such as flexible polyvinyl chloride, is injected between mating upper and lower die halves 70 and 72. When the die halves 70 and 72 are separated, as shown in FIG. 9, one or more filter housing elements 20/22 in the form of an integral strip 80 are ejected from the tooling. The strip of four filter housing elements, integrally connected by a web 80, is shown in FIGS. 8 and 9. As described supra, each filter housing element 20/22 includes a flange portion 24, domed region 30 and port 40. In addition, a carrier web 74 extends from, and in some cases connects, filter housing elements 20/22. Carrier web 74 may have one or more apertures 76 formed therein.

Figure 10:
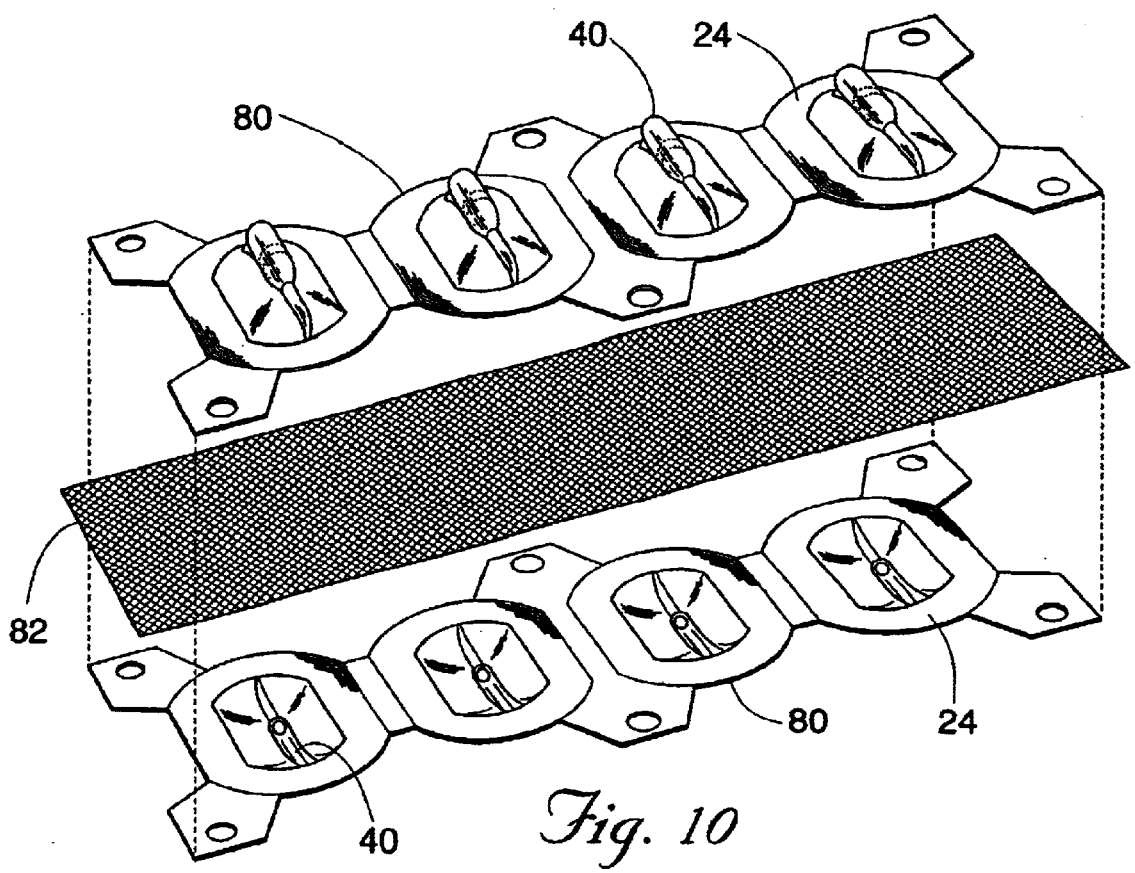
FIG. 10 is an exploded perspective view of the filter housings and filter media prior to assembly.

A method of forming a filter assembly 10 of this invention is shown in detail in FIGS. 10–13. As seen in FIG. 10, a first strip 80 of integrally connected filter housings 20/22 is placed over a filter membrane strip 82. The number of filter housings formed on strip 80 can be any desired number. A second strip of filter housings 80 is placed below the filter membrane strip 82 as shown. Ideally, the number of filter housing in first strip should be same as the number of filter housings in second strip. As best seen in FIG. 10, the orientation of the top filter housing element ports 40 is opposite the orientation of the bottom filter housing element ports 40. While this is the preferred arrangement of the housing element strips 80, the ports 40 could have the same orientation.

Figure 11:
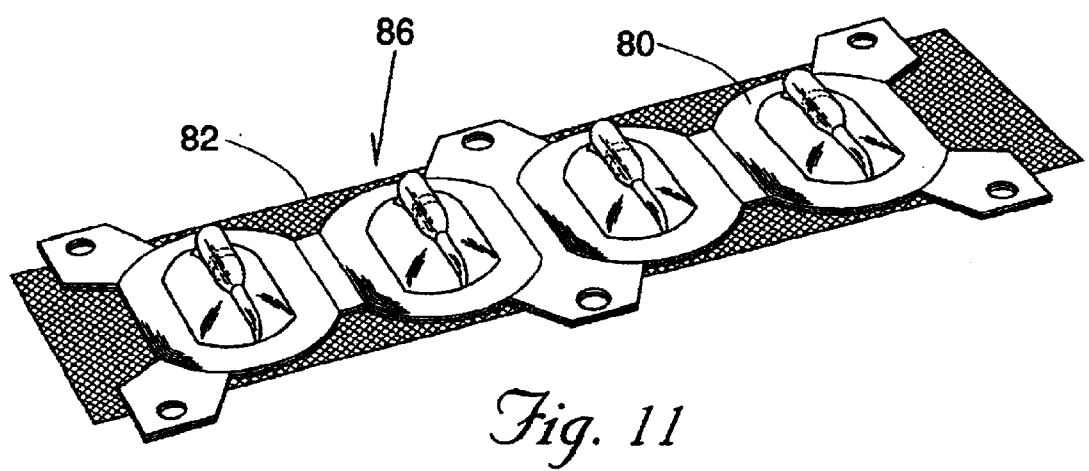
FIG. 11 is a perspective view of the filter housings and filter media prior to assembly.

The first strip 80, filter membrane 82 and second strip 80 are brought together as shown in FIG. 11 forming a pre-assembly 86. It is important to note that the filter membrane strip is sufficiently narrow and does not cover the apertures 76 formed in the first and second strips 80. It should also be noted that the apertures 76 of the first strip 80 are in alignment with the apertures 76 of the second strip 80. This insures that the flange portions 24 of the respective filter housing elements are in substantial alignment as well.

Figure 12:
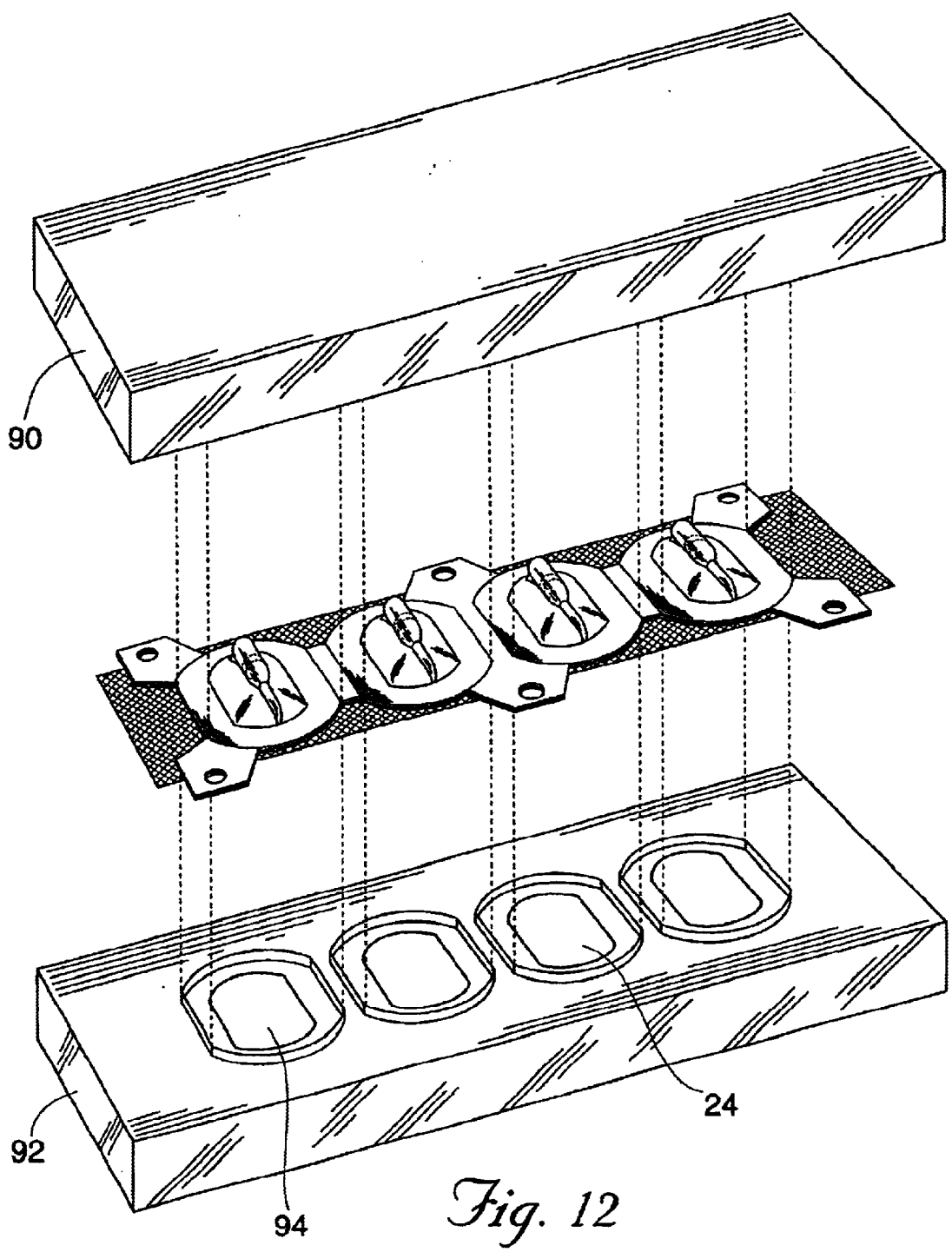
FIG. 12 is an exploded perspective view of the filter assemblies after the heating step.

As seen in FIG. 12, a pair of opposed dies 90 and 92 are positioned on opposite sides of filter housing element strip, filter membrane, filter housing element strip pre-assembly 86. Dies 90 and 92 are provided with aligned concave recesses 94 that form a pocket. While not shown, one or more mandrels may be provided on the dies for receiving the apertures in filter housing element strips 80 and positively aligning the strips prior to final assembly. Dies 90 and 92 are brought together for a predetermined amount of time. Preferably a stop is provided to accurately space dies 90 and 92 apart from each other. RF energy is then supplied through dies 90 and 92 in order to soften the thermoplastic material of the mating filter housing elements flanges 24. Dies 90 and 92, which remain relatively cool, act as a mold for the softened material. Material from the flange 24 of the first outer filter housing element 20 flows through the filter membrane strip 82. Likewise, material from the flange 24 of second outer filter housing element 22 flows through the filter membrane strip 82. The melted periphery portions 24 of housing elements 20 and 22 serve to reinforce the junction between housings 20 and 22 and the filter membrane strip 82. A depression 38 of slightly decreased thickness is formed along the conjunctive periphery surrounding each filter assembly 10. After a brief period of cooling, the softened and flowing thermoplastic material hardens sufficiently and dies 90 and 92 can be withdrawn.

RF energy is applied for the dielectric heating step through a mechanism which feeds the energy equally to each die halve. Preferably, a mechanical stop is used to ensure that the two dies are separated by 0.020 inch. Since the dies are not greatly heated by the dielectric heating, they can be withdrawn after a brief cooling period.

Figure 13:
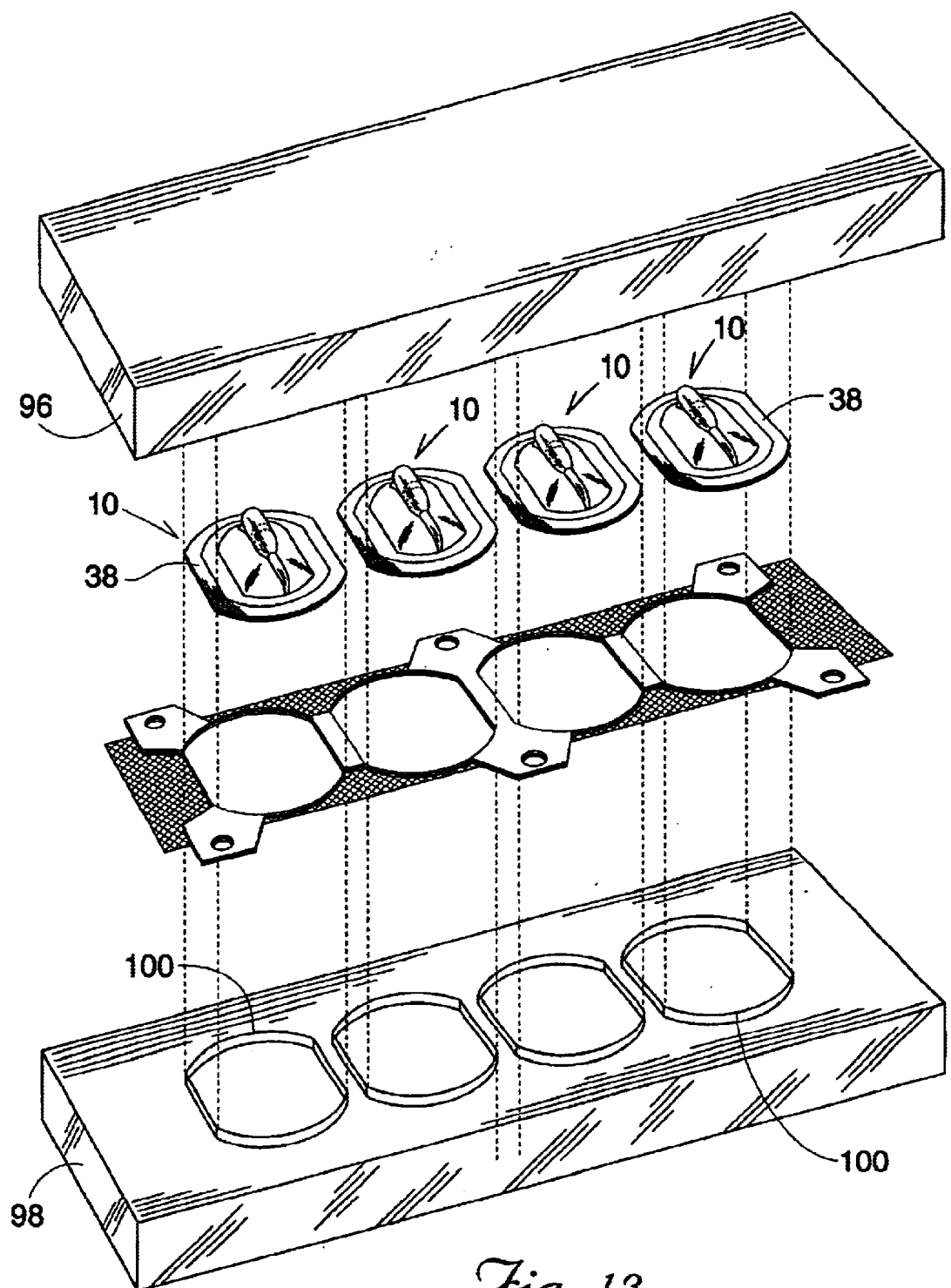
FIG. 13 is an exploded perspective view of the filter assemblies after the die cutting step.
Figure 14:
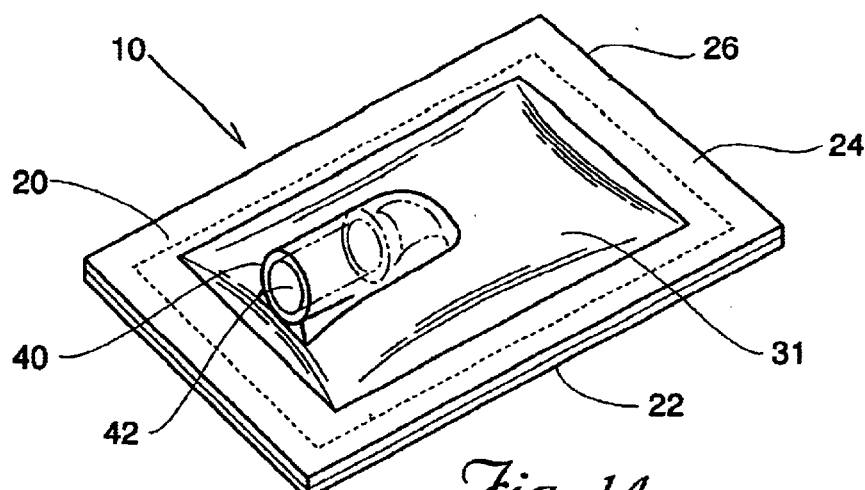
FIG. 14 is a perspective view of a second embodiment of the filter assembly.
Figure 15:
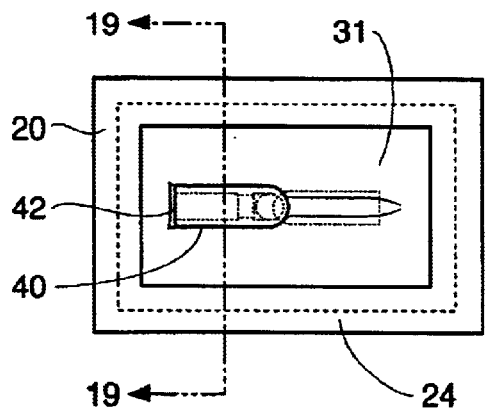
FIG. 15 is a top plan view of the filter assembly shown in FIG. 14.
Figure 16:
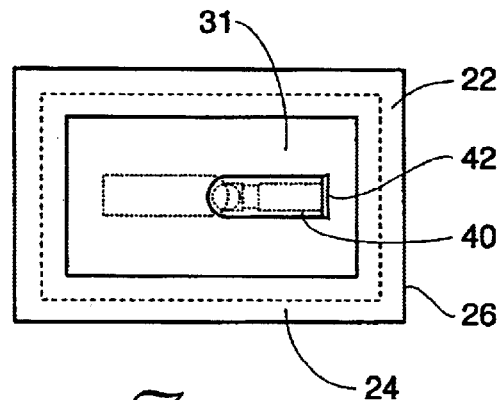
FIG. 16 is a bottom plan view of the filter assembly shown in FIG. 14.

After the assembly is thus formed by the foregoing procedure, the multiple filter assemblies are die cut as shown in FIG. 13, into individual filter assemblies. First and second cutting dies 96 and 98, commonly known in the trade, having cutting edges 100, perform the die cutting operation. A strip of assembled filter assemblies is placed between the dies 96 and 98. Again while not shown, one or more mandrels may be positioned on the dies to properly align the multiple filter assembly prior to the cutting operation.

Finally, conduits 50 and 52 can be applied to the filter assembly 10 by any known method, for example, interference fit, adhesive or solvent bonding.

Referring now to FIGS. 14 through 19, an alternative embodiment of filter assembly 10 can be seen to include first and second filter housing elements 20 and 22. As will hereinafter be appreciated, and as is apparent from FIGS. 15 and 16, the housing elements 20 and 22 are identical. Each housing element 20 and 22 includes a flange 24 formed about its periphery 26. A substantially flat flexible region 31 is formed within the flange area 24. The filter housing elements 20 and 22 are arranged, as will be described in greater detail, so that their flexible regions 31 form and define an interior filter cavity 32.

Figure 17:
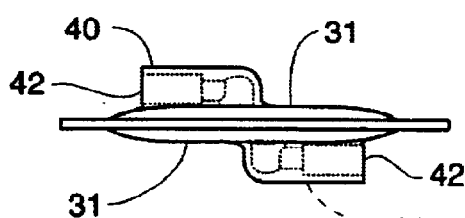
FIG. 17 is a right side elevation view of the filter assembly of the filter assembly shown in FIG. 14, the left side elevation view being a mirror image thereof.
Figure 18:
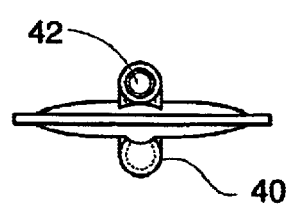
FIG. 18 is a front elevation view of the filter assembly shown in FIG. 14.

The flexible region 31 of each filter housing element 20 or 22 has at least one port 40 formed integral with the filter housing element. Port 40 includes an inlet 42 that passes though flexible region 31 and that is in fluid communication with the interior cavity 32 of the filter assembly 10. Inlet 42 is sized to receive the end of a fluid carrying conduit, such as a flexible medical grade plastic (e.g., PVC) or rubber tube or hose. As best shown in FIG. 17, a shoulder 44 is formed within each inlet 42 to act as a conduit stop. The conduit stop prevents the insertion of a conduit too far into the filter assembly thereby possibly damaging or rupturing the filter media contained therein.

Each filter housing element 20 or 22 is preferably injection molded from a flexible thermoplastic material, such as flexible PVC material. The components of each element, including the flange 24, flexible region 31, port 40 having opening 42, and conduit stop 44 are integrally molded as a single, unitary component. Unlike prior art devices, there is a minimized risk of fluid leaking at the junction of flexible portion 31 and port 40.

Figure 19:
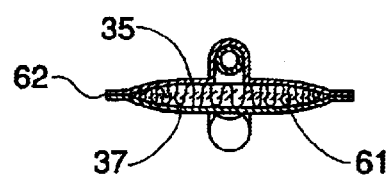
FIG. 19 is a cross sectional view taken along line 19—19 in FIG. 15 showing the filter media within the filter assembly.

An example of a filtration medium that may be sealed within the interior cavity 32 is best shown in FIG. 19. As shown, a filtration medium 61 having a periphery 62 is arranged and sealed between filter housing elements 20 and 22. The filtration medium may include polyester mesh, cotton wool, cellulose acetate or another synthetic fiber like polyester.

In a preferred alternative embodiment, filter membrane 61 is heat sealed between the respective flanges 24 of housing element 20 and housing element 22 to form the interior region 32. The interior region 32 can be further divided into a first half 35 defined by housing element 20 and a first side 62 of filter membrane 61 and a second half 37 defined by housing element 22 and a second side 64 of filter membrane 61. It is to be understood that the filtration medium need not be sealed within the periphery of the filter device, but may simply be located within the interior region 32.

In use a fluid, such as whole blood, flows through opening 42 in port 40 formed in first or upper filter housing 20. The fluid then flows into first half 35, through filter media 61 and into second half 37. The fluid exits the filter assembly 10 by flowing through the opening 42 formed in port 40 of filter housing 22. The depicted alternative embodiment of the filter assembly 10 shows the location of each filter ports 40 is formed substantially tangentially to the wall of the flexible portion 31. The type of fluid to be filtered, whether or not the filter assembly must trap air within its interior region and the physical constraints of the filter application may dictate the orientation and location of port 40. It is to be understood that different locations and orientations of the port 40 may be made without deviating from the invention.

It is, thus, appreciated that the port 42 is formed in each filter housing element 20 generally tangential or parallel to the wall of the element. In the case of a filter device 10, the available surface area of the filtration medium 61 is maximized since the filter membrane itself extends to or near the periphery of the filter housing interior cavity 32 without adversely affecting fluid flow in and out of the filter assembly.

The filter assembly 10 of this alternative embodiment is also flexible and thus capable of collapsing and expanding depending upon the fluid or combination of fluids flowing through the filter assembly. For example, if both a liquid, such as blood, and air are simultaneously flowing through a non-flexible or rigid filter assembly, a phenomenon known as foaming is likely to occur. The present invention 10 prevents this phenomenon by its ability to collapse when the volume of a non-compressible fluid (e.g. liquid) is decreased. Decreasing the volume of the interior cavity 32 prevents the foaming phenomenon from occurring.

It is preferred that the outer filter housings 20 and 22 be injection molded of flexible PVC material which is selected because of its receptiveness to dielectric heat sealing. Any suitable material can be modified by addition of various plasticizers and readily sterilized using conventional sterilization methods.

In a preferred example of the invention, filter housing elements 20/22 are injection molded from flexible polyvinyl chloride. The injection molding dies provide for a uniform wall thickness of 0.020 inches.

The present invention 10 may also be utilized in manual blood collection assemblies for removing undesirable materials, e.g., leukocytes, from red blood cells, platelet-rich plasma, platelet-poor plasma, or platelet concentrate. A description of representative blood collection assemblies is set forth below.

Figure 20:
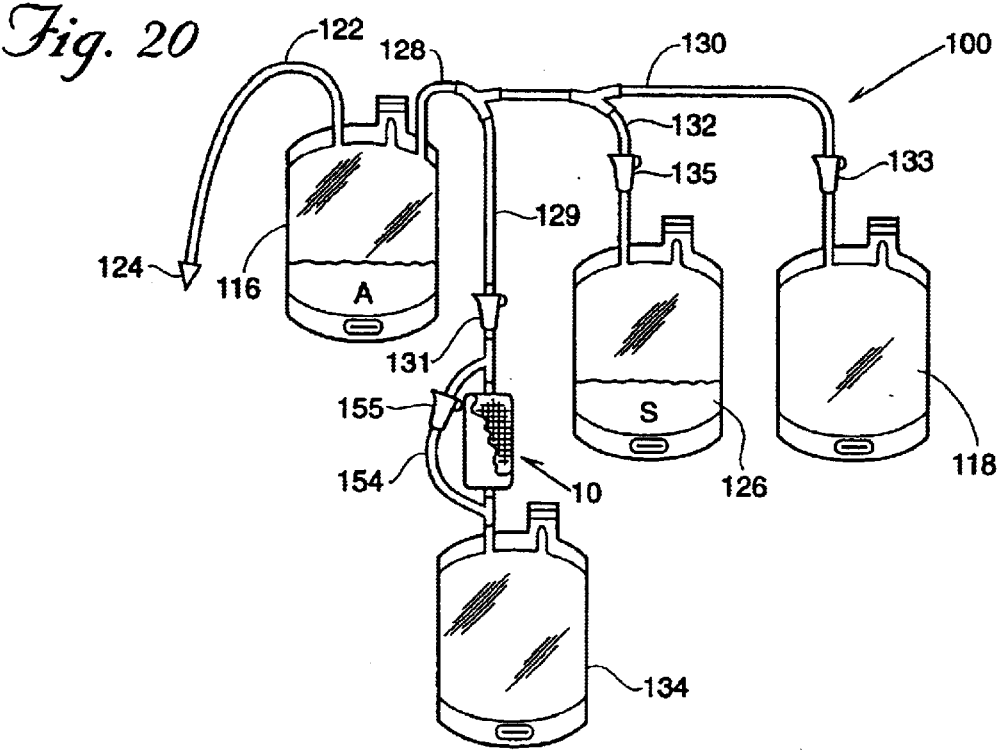
FIG. 20 is a schematic view of a red blood cell collection system including the present invention.

One representative blood collection assembly 100 for removing undesirable materials, e.g., leukocytes, from red blood cells is shown in FIG. 20. The assembly 100 comprises a closed manual blood collection system. In the illustrated embodiment, the assembly 100 serves to separate and store the red blood cells as well as the plasma and platelet blood components by conventional centrifugation techniques, while removing undesired matter from the red blood cells prior to storage. In the illustrated embodiment, the undesired matter is removed generally by filtration and specifically utilizing the filter device described herein.

In the illustrated system shown in FIG. 20, the assembly 100 includes a primary bag or container 116 and various transfer bags or containers 118, 126, and 134 that are attached to the primary bag 16 by integrally attached branched tubing 128. The tubing 128 is divided by appropriate connectors into branches 129, 130, and 132.

In the illustrated embodiment, flow control devices 131, 133, and 135 are provide on the branched fluid flow paths as shown to enable directing of the fluid transfers in a desired sequence of steps. In the illustrated arrangement, the flow control devices take the form of conventional roller clamps that are manually operated to open and close the associated tubing paths.

In use, the primary bag 116 (which is also called a donor bag) receives whole blood from a donor through integrally attached donor tubing 122 that carries an phlebotomy needle 124. A suitable anticoagulant A is contained in the primary bag 116.

The transfer bag 126 contains a suitable storage solution S for the red blood cells. One such solution is disclosed in Grode et al U.S. Pat. No. 4,267,269. Another solution is sold under the brand name ADSOL®.

The transfer bag 118 is intended to receive the platelet and plasma blood components associated with the whole blood collected in the primary bag 116. The transfer bag 118 ultimately serves as the storage container for the platelet concentrate constituent. The transfer bag 126 also ultimately serves as the storage container for the platelet-poor plasma constituent.

Flow control device 133 is located in tubing 130 to control fluid flow to and from the transfer bag 118. Flow control device 135 is located in tubing 132 to control fluid flow to and from transfer bag 126.

Tubing 128 and 129 form a flow path to the container 134. This flow path includes the filter device 10 of the present invention for separating undesired matter from blood cells. Flow control means 131 is located on tubing 129 that leads to the filter 10. The container 134 ultimately serves as a storage container for the red blood cells after passage through the filter device 10.

The bags and tubing associated with the processing assembly 100 can be made from conventional approved medical grade plastic materials, such as polyvinyl chloride plasticized with di-2-ethylhexyl-phthalate (DEHP). The ends of the tubing may be connected by "Y" or "T" connectors to form the branched fluid flow paths.

Alternatively, transfer container 118, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

The blood collection and storage assembly 100, once sterilized, constitutes a sterile, "closed" system, as judged by the applicable standards in the United States.

Figure 21:
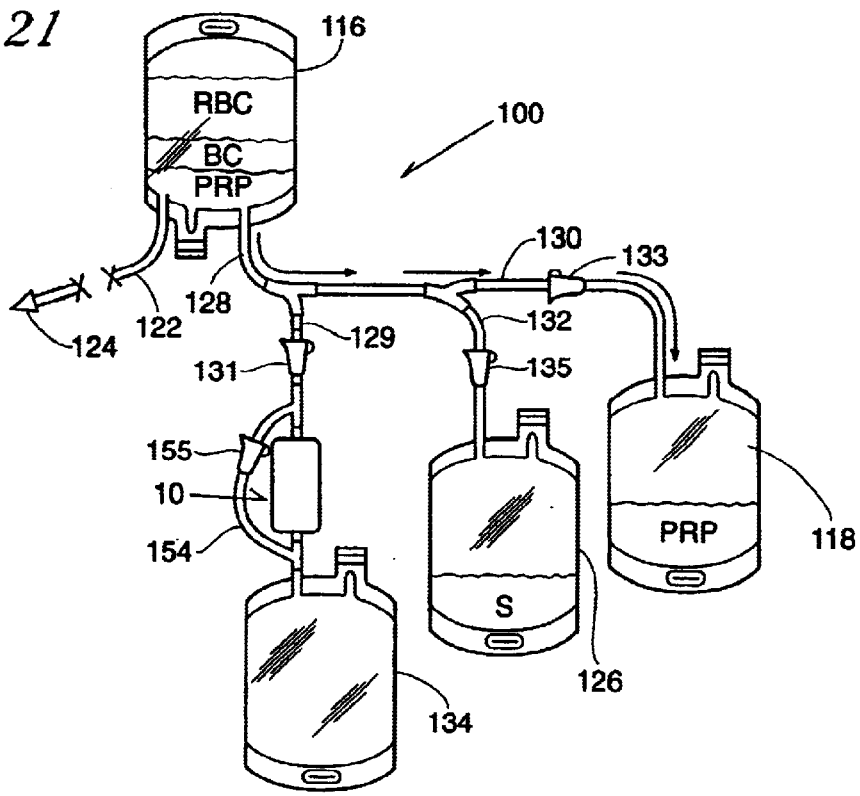
FIG. 21 is a schematic view of the system shown in FIG. 20 being used to transfer platelet-rich component to an associated transfer assembly.

When the system 100 is used, whole blood is collected in the primary bag 116. The collected whole blood is centrifugally separaed within the primary bag 116 into a red blood cell component (designated RBC in FIG. 21) and platelet-rich plasma component (designated PRP in FIG. 21). During such separation techniques, a layer of leukocytes (commonly called the "buffy coat" and designated BC in FIG. 21) forms between the red blood cells and the platelet-rich plasma.

In a first processing mode (shown in FIG. 21), the platelet-rich plasma component is transferred by conventional techniques from the primary bag 116 to the transfer bag 118. This transfer is accomplished by opening clamp 133, while closing clamps 131 and 135. In this step, attempts are made to keep as many leukocytes in the primary bag 116 as possible. The transfer of platelet-rich plasma into the first transfer bag 118 leaves the red blood cells and the remaining leukocytes behind in the primary bag 116.

Figure 22:
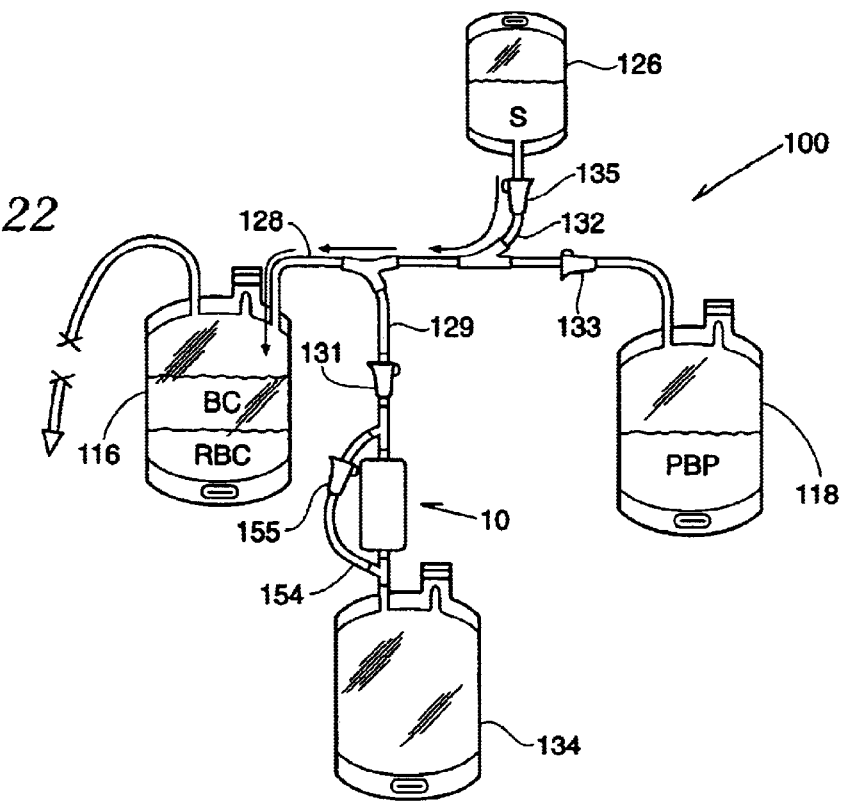
FIG. 22 is a schematic view of the system shown in FIG. 20 being used to transfer an additive solution from the associated transfer assembly into the red blood cells in the primary collection container.

In a second processing mode (shown in FIG. 22), the solution S is transferred from the transfer bag 126 into the primary bag 116. This transfer is accomplished by closing clamps 131 and 133, while opening clamp 135.

In a third processing mode (shown in FIG. 23), the mixture of additive solution S and the red blood and leukocytes in the primary bag 116 is transferred into the transfer bag 134 through the filter device 10. This transfer is accomplished by closing the clamps 133, 135 and 155 while opening the clamp 131. The red blood cells and additive solution S enter the container 134 essentially free of leukocytes.

It should be appreciated that the filtration medium within the filter device housing 20/22 can be used to remove all types of undesired materials from different types blood cells, depending upon its particular construction. In the illustrated embodiment, the filter device 10 is intended to remove leukocytes from the red blood cells prior to storage. For example, the filtration medium 60 located within housing 20/22 can include cotton wool, cellulose acetate or another synthetic fiber like polyester. The undesired matter is removed from the red blood cells by the filter device 10.

Figure 23:
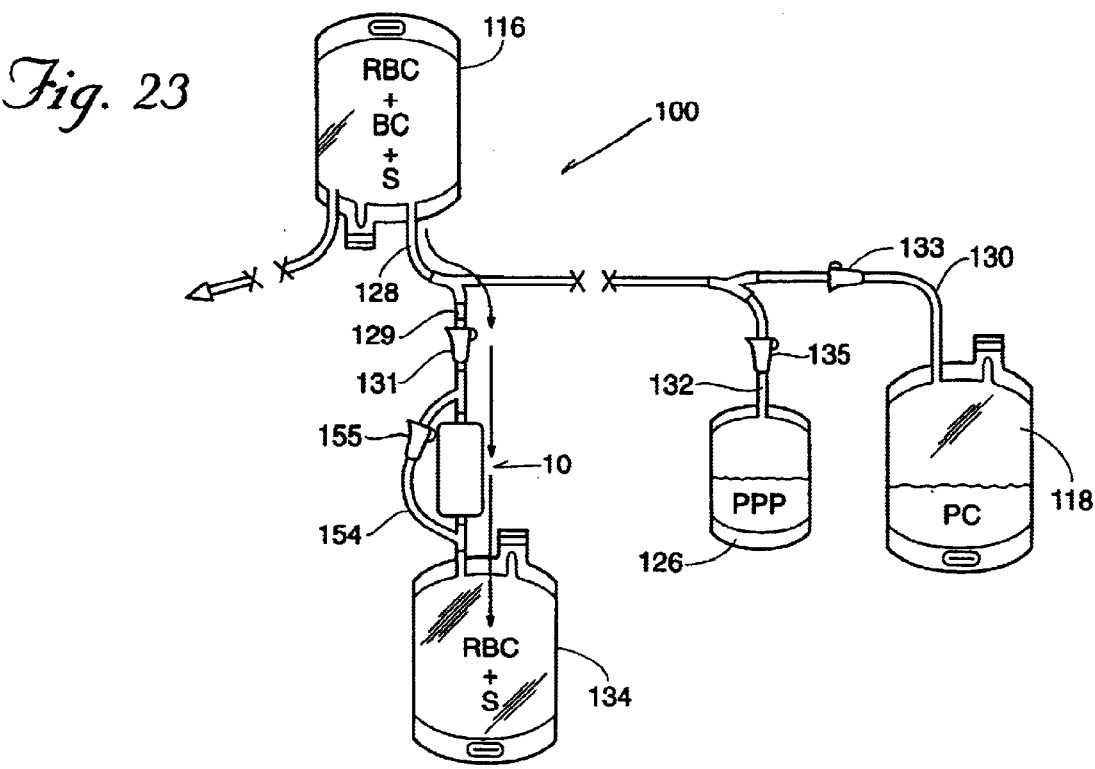
FIG. 23 is a schematic view of the system shown in FIG. 20 being used to remove undesired matter from the red blood cells in another transfer assembly, while platelet and plasma separation occurs in the now separated first transfer assembly.

In a fourth processing mode (shown in FIGS. 23 and 24), a constituent of the component contained in the transfer bag 118 is transferred to the transfer bag 126. In the illustrated embodiment, this processing mode is accomplished by first separating the transfer bags 118 and 126 from the system 100 (as FIG. 23 shows). The separation of the bags is accomplished by forming snap-apart seals in the tubing 130 that makes up the branched fluid flow path 130 leading to the transfer bags 118 and 126. A conventional heat sealing device (for example, the Hematron® dielectric sealer sold by Baxter Healthcare Corporation) can be used for this purpose. This device forms a hermetic, snap-apart seal in the tubing 130 (this seal is schematically shown by an "x" in FIGS. 23 and 24). Preferably, the donor tubing 122 is also sealed and disconnected in the same fashion (as shown in FIG. 23).

Figure 24:
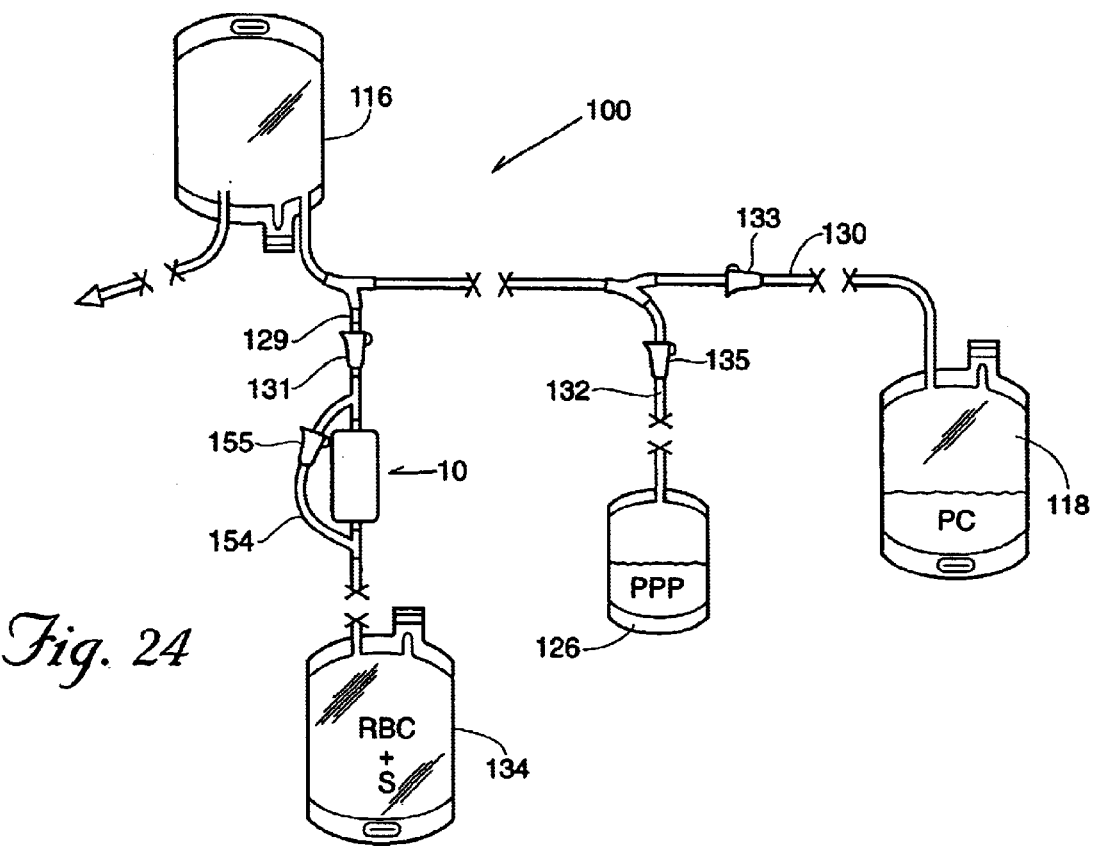
FIG. 24 is a schematic view of the system shown in FIG. 20 with all the associated storage containers separated for the storage of individual components.

Once separated, the platelet-rich plasma undergoes subsequent centrifugal separation within the transfer bag 118 into platelet concentrate (designated PC in FIGS. 23 and 24) and platelet-poor plasma (designated PPP in FIGS. 23 and 24). The platelet-poor plasma is transferred into the transfer bag 126 (by opening the clamps 133 and 135), leaving the platelet concentrate in the first transfer bag 118.

As FIG. 24 shows, the bags 118 and 126 are then themselves separated by forming snap-apart seals "x" in the tubing 130 for subsequent storage of the collected components. The transfer bag 134 (containing the filtered red blood cells) is also separated in the same fashion for storage (as FIG. 24 also shows).

Should air become trapped in the transfer bag 134, it may be necessary to transfer the air through path 128 into the primary bag 116 before separating the transfer bag 134 from the system 100. As seen in FIGS. 20–24, an air bleed channel 154 can be incorporated on either side of the filter device 10 for this purpose. Means such as a clamp 155 can be provided to open and close bypass line 154 as required. Clamp 131 is opened during this step to allow the vented air to proceed into the primary bag 116. To alternatively prevent flow of the blood cells being filtered through this channel in the filtration step, a suitable one-way valve (not shown) may be provided within the filter device 10 to close the end of the channel near the inflow opening to filter device 10.

Figure 25:
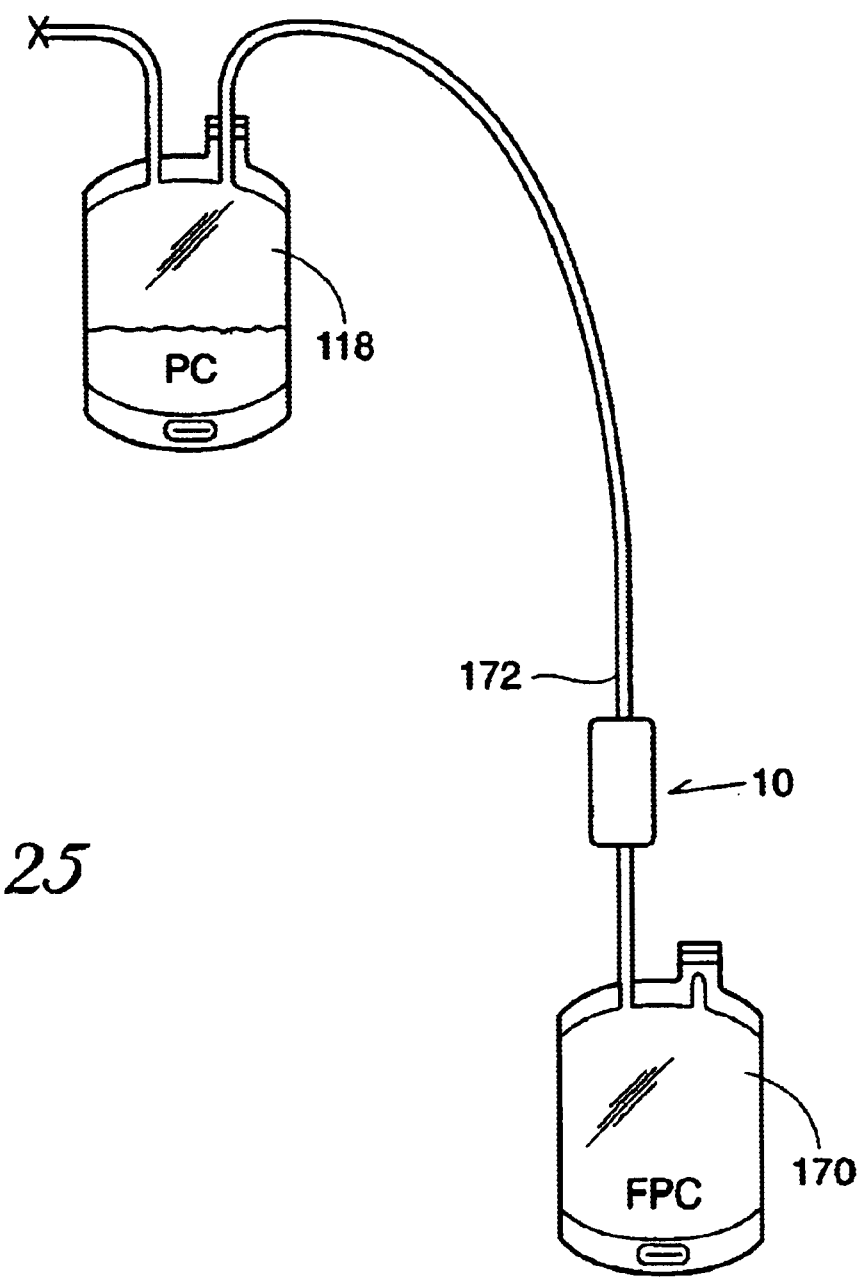
FIG. 25 is a schematic view of an additional filtering step utilizing the system shown in FIG. 20 being used to remove undesired matter from the platelet concentrate.

In an optional fifth processing mode and now referring to FIG. 25, the platelet concentrate remaining in first transfer bag 118 may be filtered through a separate filter device 10 to remove leukocytes and yield filtered platelet concentrate (designated FPC in FIG. 25). A fifth transfer bag 170 is attached to transfer bag 118 by tubing 172. Tubing 172 forms a flow path from transfer bag 118 to transfer bag 170. The flow path includes a separate or second inline filter device 10 for separating the undesired matter from the platelet concentrate. If desired a flow control device, such as a roller clamp (not shown), may be provided on the tubing 172. The transfer bag 170 ultimately serves a storage container for the filtered platelet concentrate after passage through the filter device 10.

Figure 26:
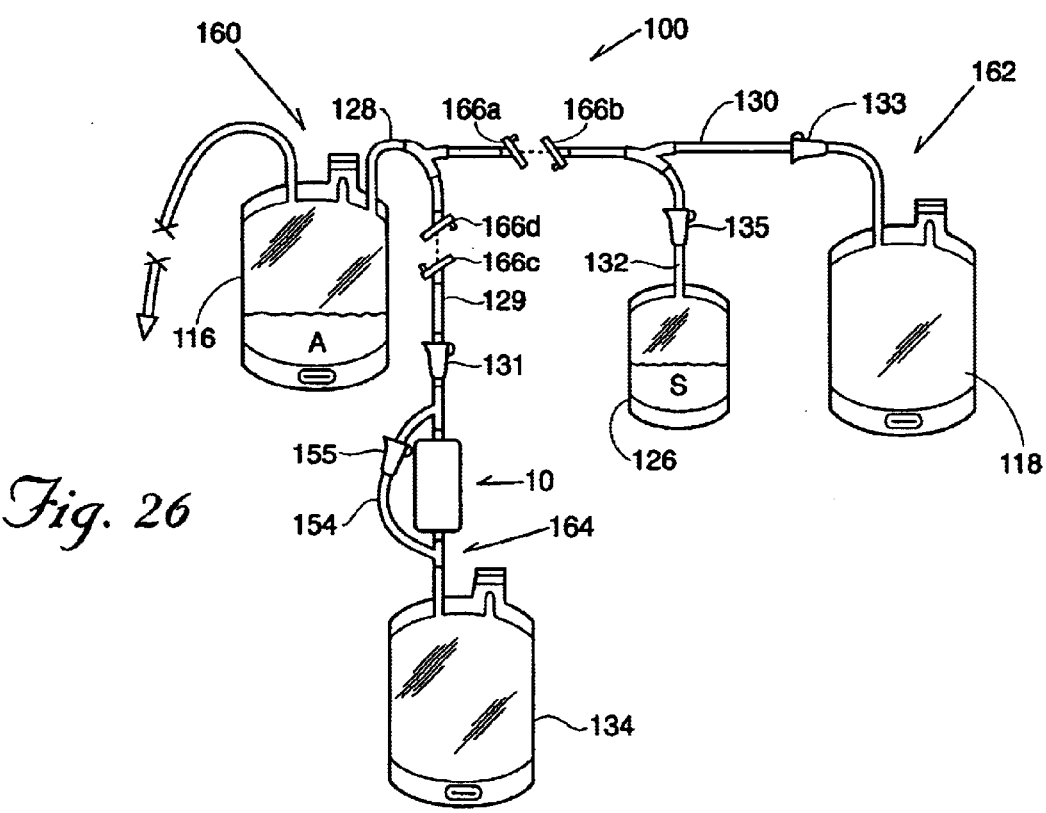
FIG. 26 is a schematic view of an alternative arrangement of the system shown in FIG. 20, in which the various assemblies comprise initially separate subassemblies that are joined together at time of use.

In the embodiment shown in FIG. 26, the system 100 comprises three initially separate subassemblies 160, 162 and 164. The subassembly 160 constitutes a blood collection assembly and includes the primary bag 116 and integrally joined tubing 128. The subassembly 162 constitutes a first transfer assembly and includes the transfer bags 118 and 126 with integrally joined tubing 130 and 132 (with associated roller clamps 133 and 135). The subassembly 164 constitutes a second transfer assembly and includes the transfer bag 134, the filter device 10, and the tubing 129 (with associated roller clamp 131).

The separate subassemblies 160, 162, and 164 are joined together at time of use to comprise the system 100 shown in FIG. 20. For this purpose, the embodiment shown in FIG. 26 includes a means for connecting the initially separate subassemblies 160, 162, and 164 together. The connection means is associated with each of the initially separate subassemblies 160, 162, and 164.

In the embodiment shown in FIG. 26, the connection means comprises mating sterile connection devices (designated 166a, 166b, 166c and 166d). The devices 166a, 166b, 166c, and 166d are described in Granzow et al U.S. Pat. Nos. 4,157,723 and 4,265,280, which are incorporated herein by reference.

The tubing 128 of the subassembly 160 carries the devices 166a and 166d. The tubing 130 of the transfer subassembly 162 carries the device 166b. The tubing 129 of the transfer subassembly 164 carries the device 166c.

The devices 166a, 166b, 166c, and 166d normally close the associated assemblies 160, 162, and 164 from communication with the atmosphere and are opened in conjunction with an active sterilization step which serves to sterilize the regions adjacent to the interconnecting fluid path as the fluid path is being formed. These devices 166a, 166b, 166c, and 166d also hermetically seal the interconnecting fluid path at the time it is formed. The use of these sterile connection devices 166a, 166b, 166c, and 166d assures a probability of non-sterility that exceeds one in a million. The devices 166a, 166b, 166c, and 166d thus serve to connect the subassemblies 160, 162, and 164 without compromising their sterile integrity.

Alternately, the connection means can comprise the sterile connecting system disclosed in Spencer U.S. Pat. No. 4,412,835 (not shown). In this arrangement, this system forms a molten seal between the tubing ends. Once cooled, a sterile weld is formed.

The subassemblies 160, 162, and 164, once sterilized, each constitutes a sterile, "closed" system, as judged by the applicable standards in the United States.

Figure 27:
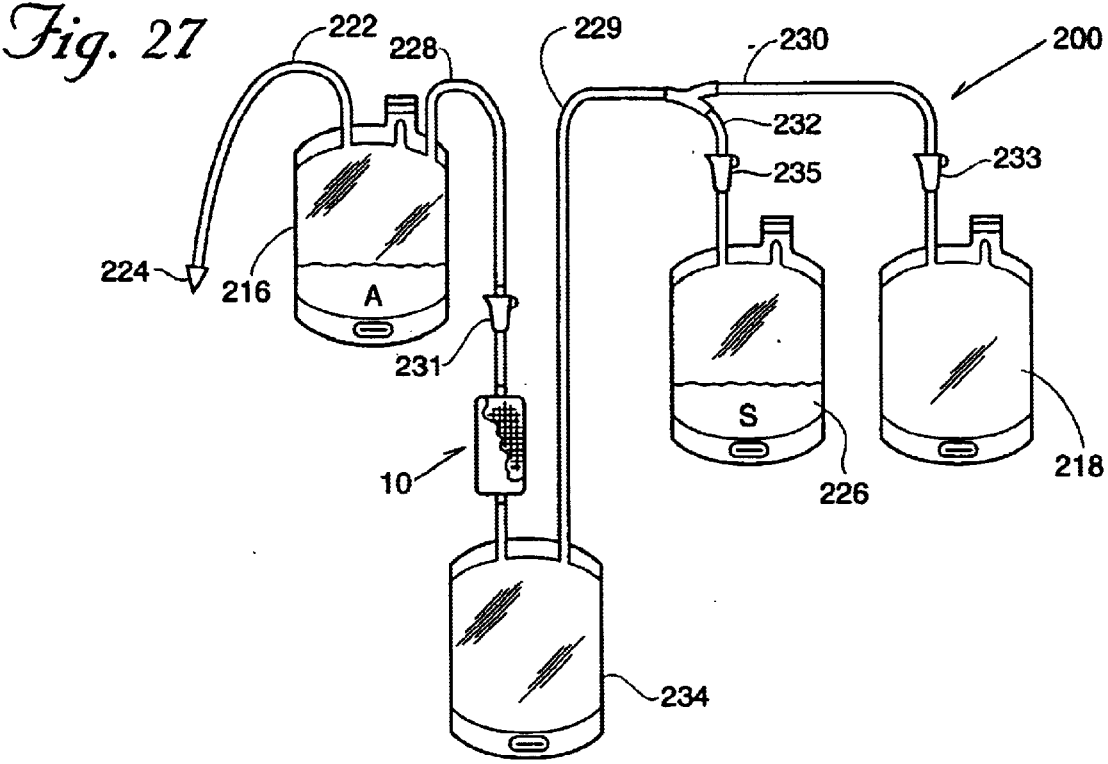
FIG. 27 is a schematic view of a white blood cell collection system including the present invention.

A blood collection system 200 for removing undesirable material, e.g., leukocytes, from whole blood prior to centrifugal processing is shown in FIG. 27. Again, the assembly comprises a closed blood collection system. In the illustrated embodiment, the assembly 200 serves to separate and store red blood cells as well as plasma or plasma-platelet blood components by conventional centrifugation techniques, while removing undesirable material such as leukocytes prior to storage. In the illustrated embodiment, the undesired matter is removed generally by filtration and specifically utilizing the filter device 10 described herein.

In the illustrated embodiment shown in FIG. 27, the assembly 200 includes a primary bag or container 216 and various transfer bags or containers 218, 226, and 234. Transfer bag 234 is attached to the primary bag 216 by integrally attached tubing 228. Transfer bags 218 and 234 are attached to transfer bag 234 by integrally attached tubing 229. The tubing 229 is divided by appropriate connectors into branches 230 and 232.

In the illustrated embodiment, flow control devices 231, 233, and 235 are provided on the branched fluid flow paths as shown to enable directing of the fluid transfers in a desired sequence of steps. In the illustrated arrangement, the flow control devices take the form of conventional roller clamps that are manually operated to open and close the associated tubing paths.

In use, the primary bag 216 (which is also called a donor bag) receives whole blood from a donor through integrally attached donor tubing 222 that carries an phlebotomy needle 224. A suitable anticoagulant A is contained in the primary bag 216.

The transfer bag 226 contains a suitable storage solution S for the red blood cells. One such solution is disclosed in Grode et al U.S. Pat. No. 4,267,269. Another solution is sold under the brand name ADSOL®.

The transfer bag 218 is intended to receive the plasma components associated with the whole blood collected in the primary bag 216. The plasma component may also contain platelets and comprise platelet-rich plasma, if the media in the filter device 10 has the characteristic of allowing platelets to pass. Otherwise, the plasma component comprises platelet-poor plasma. The transfer bag 218 ultimately serves as the storage container for the platelet constitent contained in the plasma constituent. In this arrangement, the transfer bag 226 also ultimately serves as a storage container for the plasma constituent. The transfer bag 234 also ultimately serves as the storage container for the red blood cell constituent.

Flow control device 233 is located in tubing 230 to control fluid flow to and from the transfer bag 218. Flow control device 235 is located in tubing 232 to control fluid flow to and from transfer bag 226.

Tubing 228 forms a flow path from donor bag 216 to the container 234. This flow path includes the filter device 10 of the present invention for separating undesired matter such as leukocytes from the whole blood collected in the primary bag 216. Flow control means 231 is located on tubing 228 that leads to the filter 10.

The bags and tubing associated with the processing assembly 200 can be made from conventional approved medical grade plastic materials, such as polyvinyl chloride plasticized with di-2-ethylhexyl-phthalate (DEHP). The ends of the tubing may be connected by "Y" or "T" connectors to form the branched fluid flow paths.

Alternatively, transfer container 218, which is intended to store the platelet constitent, can be made of polyolefin material (as disclosed in Gajewski et al U.S. Pat. No. 4,140,162) or a polyvinyl chloride material plasticized with tri-2-ethylhexyl trimel-litate (TEHTH). These materials, when compared to DEHP-plasticized polyvinyl chloride materials, have greater gas permeability that is beneficial for platelet storage.

It should be appreciated that the filtration medium within the filter device housing 20/22 can be used to remove all types of undesired materials from different types blood cells, depending upon its particular construction. In the illustrated embodiment, the filter device 10 is intended to remove leukocytes from whole blood cells prior to centrifugation in the transfer bag 234. The media of the filter device 10 may also remove platelets, if desired. For example, the filtration medium 60 located within housing 20/22 can include polyester mesh, cotton wool, cellulose acetate or another synthetic fiber like polyester.

After filtration, the bags 216 and 234 are separated by forming snap-apart seals "x" in the tubing 228. The separation of the bags is accomplished by forming snap-apart seals in the tubing 228 that makes up the branched fluid flow paths leading to the transfer bags. A conventional heat sealing device (for example, the Hematron® dielectric sealer sold by Baxter Healthcare Corporation) can be used for this purpose. This device forms a hermetic, snap-apart seal in the tubing (this seal is schematically shown by an "x" in FIG. 28).

Figure 28:
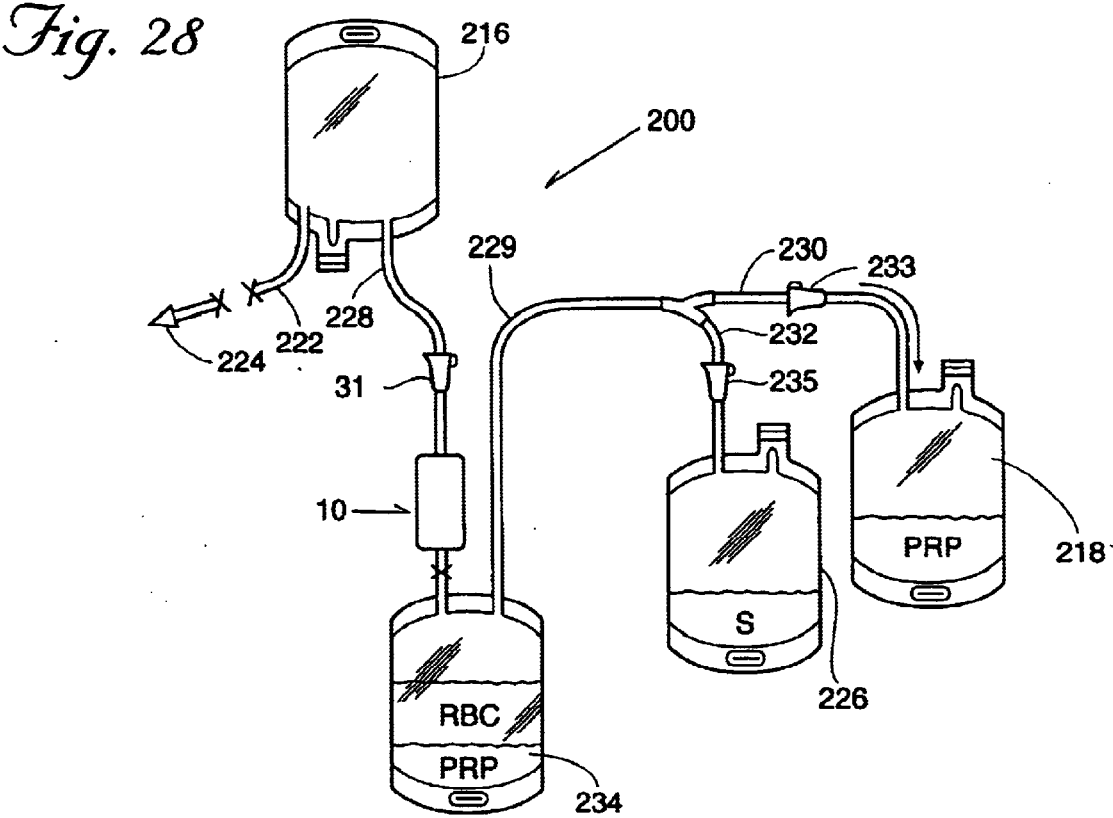
FIG. 28 is a schematic view of the system shown in FIG. 27 being used to transfer whole blood to an associated transfer assembly.

In a first processing mode (shown in FIG. 28), the filtered whole blood within the transfer bag 234 is centrifugally separated within the transfer bag 234 into a red blood cell component (designated RBC in FIG. 28) and a plasma constituent, which, in the illustrated embodiment, is platelet-rich plasma component (designated PRP in FIG. 28).

The platelet-rich plasma component is transferred by conventional techniques from the transfer bag 234 to the transfer bag 218. This transfer is accomplished by opening clamp 233, while closing clamp 235. The transfer of platelet-rich plasma into the transfer bag 218 leaves the red blood cells behind in the transfer bag 234.

Figure 29:
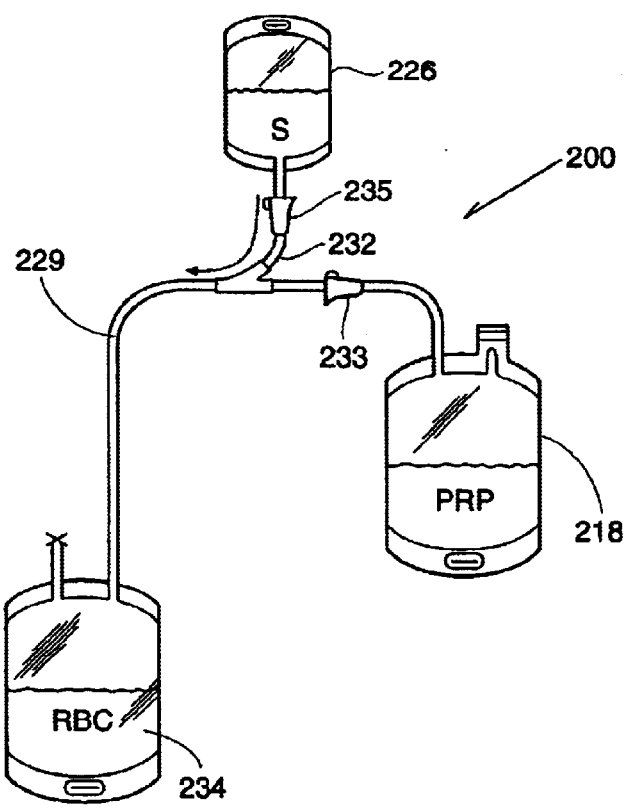
FIG. 29 is a schematic view of the system shown in FIG. 27 being used to transfer an additive solution from the associated transfer assembly into the red blood cells in the primary collection container.

In a second processing mode (shown in FIG. 29), the solution S is transferred from the transfer bag 226 into the transfer bag 234. This transfer is accomplished by closing clamp 233, while opening clamp 235.

Figure 30:
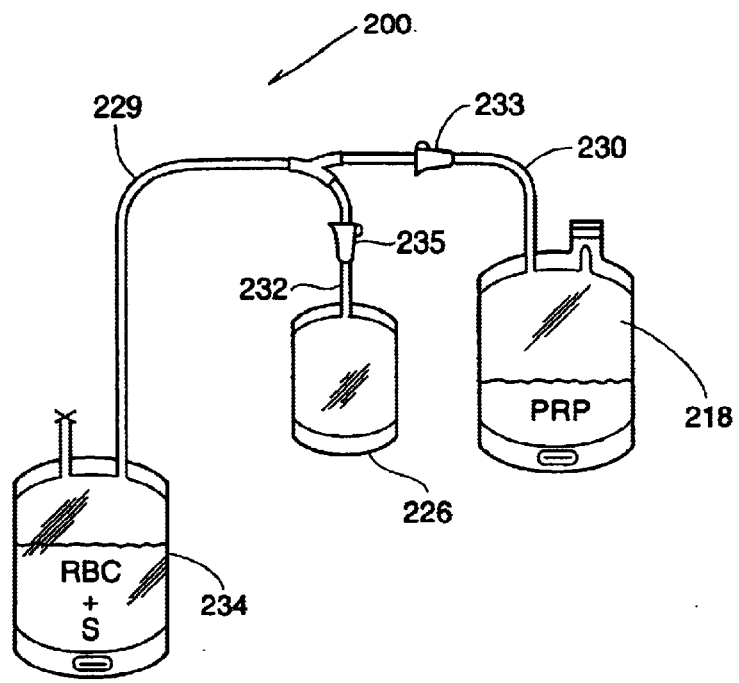
FIG. 30 is a schematic view of the system shown in FIG. 27 being used to transfer red blood cells into a transfer assembly.

In a third processing mode (not shown), the red blood cells may be transferred by conventional techniques from the transfer bag 234 to the transfer bag 226 for storage. This transfer is accomplished by opening clamp 235, while closing clamp 233. However, in the illustrated embodiment (shown in FIG. 30), where platelet concentrate is desired, the red blood cells and storage solution are left in the transfer bag 234 for storage, leaving the transfer bag 226 open to receive platelet-poor plasma constituent in the course of subsequent processing.

Figure 31:
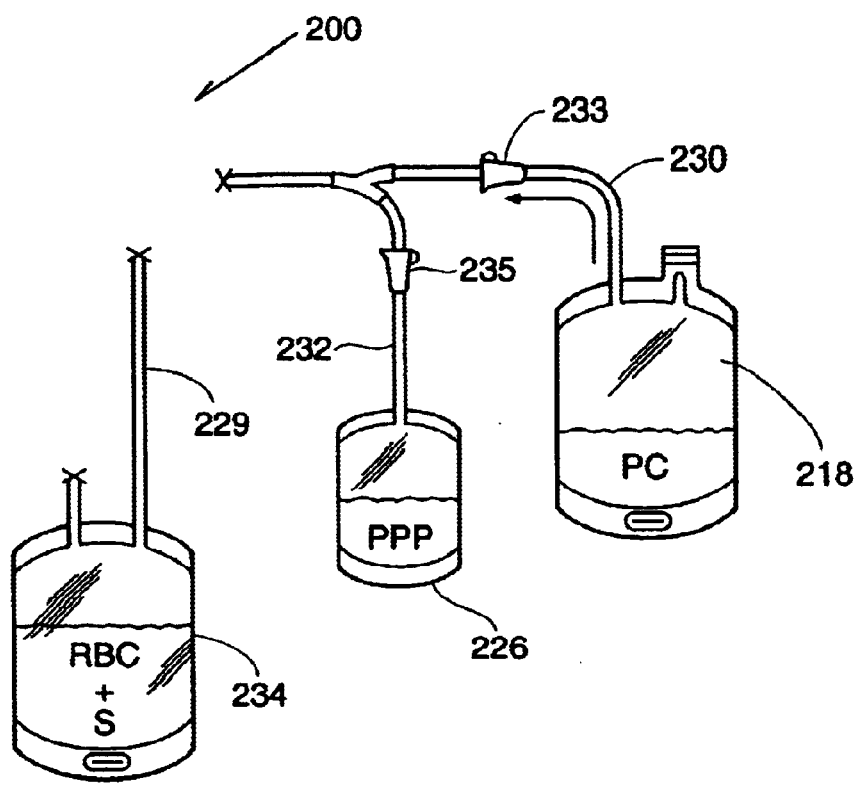
FIG. 31 is a schematic view of the system shown in FIG. 27 with all the associated storage containers separated for the storage of individual components.

In this arrangement, as FIG. 31 shows, the bags, 218 and 226 are then themselves separated from the bag 234 by forming snap-apart seals "x" in the tubing 229. The separated bags 218 and 226 are then placed in a centrifuge to separate the platelet-rich plasma in the bag 218 into platelet concentrate and platelet-poor plasma. The platelet poor plasma is expressed from the bag 218 into the bag 226, leaving the platelet concentrate in the bag 218 for long term storage.

Other modifications of the invention within the ability of those skilled in the art can be made without departing from the true scope of the appended claims.

What is claimed is:

1. A filter device comprising:

first and second flexible housing elements, each made from a thermoplastic material, a molded inlet port carried by the first flexible housing element, a molded outlet port carried by the second flexible housing element, a filter medium located between the first and second flexible housing elements, and a peripheral seal formed by application of radio frequency heating and pressure to join the first and second flexible housing elements directly to the filter medium and encapsulate the filter medium between the first and second flexible housing elements.

2. A filter device according to claim 1 wherein the inlet port is carried by the first flexible housing element spaced from the peripheral seal, and wherein the outlet port is carried by the second flexible housing element spaced from the peripheral seal.

3. A blood collection system comprising a container for holding blood, a blood filter device as defined in claim 1 or 2, and tubing connecting the blood filter device to the container.

* * * * *